United States Patent
Homanfar et al.

(10) Patent No.: US 7,817,040 B2
(45) Date of Patent: *Oct. 19, 2010

(54) RFID TRANSDUCER ALIGNMENT SYSTEM

(75) Inventors: Ramin Homanfar, Reno, NV (US);
Bela Incze, Reno, NV (US); David Massey, Sparks, NV (US)

(73) Assignee: ABR, LLC, Reno, NV (US)

( * ) Notice: Subject to any disclaimer, the term of this patent is extended or adjusted under 35 U.S.C. 154(b) by 42 days.

This patent is subject to a terminal disclaimer.

(21) Appl. No.: 12/233,430

(22) Filed: Sep. 18, 2008

(65) Prior Publication Data

US 2009/0052618 A1 Feb. 26, 2009

Related U.S. Application Data

(63) Continuation of application No. 11/959,249, filed on Dec. 18, 2007, now Pat. No. 7,518,518, which is a continuation of application No. 11/205,348, filed on Aug. 16, 2005, now Pat. No. 7,319,396.

(60) Provisional application No. 60/602,223, filed on Aug. 16, 2004, provisional application No. 60/602,751, filed on Aug. 18, 2004.

(51) Int. Cl.
*G08B 13/14* (2006.01)
(52) U.S. Cl. .................. 340/572.1; 340/686.2; 378/170
(58) Field of Classification Search ............. 340/572.1, 340/686.2–686.4, 945, 960, 967; 700/57; 701/6, 14; 702/150; 73/178 R, 179, 147; 244/1 R, 99.11; 378/168, 170
See application file for complete search history.

(56) References Cited

U.S. PATENT DOCUMENTS

| | | | |
|---|---|---|---|
| 3,548,209 A | 12/1970 | Smith | |
| 4,012,638 A | 3/1977 | Altschuler et al. | |
| 4,334,135 A | 6/1982 | Smith | |
| 4,564,355 A | 1/1986 | Traiger et al. | |
| 4,864,294 A | 9/1989 | Fukuhisa | |
| 5,068,887 A | 11/1991 | Hughes | |
| 5,757,021 A | 5/1998 | Dewaele | |
| 5,828,722 A | 10/1998 | Ploetz et al. | |
| 5,874,896 A | 2/1999 | Lowe et al. | |
| 6,047,257 A | 4/2000 | Dewaele | |

(Continued)

FOREIGN PATENT DOCUMENTS

CA 2016602 11/1991

(Continued)

*Primary Examiner*—John A Tweel, Jr.
(74) *Attorney, Agent, or Firm*—Seed IP Law Group PLLC

(57) ABSTRACT

A radio frequency identification (RFID) system having the capacity to detect conditions of alignment, wherein the system may be used with hand-held, fixed-in-place, stationary, and permanently mounted apparatus. The system includes an RF interrogator configured for use with dental x-ray, medical imaging, film, and digital radiography apparatus, and may include a multiplicity of RF transponders or interrogators. An RF interrogator, an RF transponder, and an x-ray sensitive imaging device, and its holder are configured to be critically aligned to a dental x-ray machine head apparatus, rendering repeat imaging unnecessary. The x-ray emitter may be further configured to automatically obtain a desired x-ray image or configured so that the device cannot activate and provide a radiograph until alignment with the transponder and associated x-ray sensitive imaging device has occurred.

26 Claims, 14 Drawing Sheets

U.S. PATENT DOCUMENTS

| | | |
|---|---|---|
| 6,261,247 B1 | 7/2001 | Ishikawa et al. |
| 6,359,628 B1 | 3/2002 | Buytaert |
| 6,490,473 B1 | 12/2002 | Katznelson et al. |
| 6,545,612 B1 | 4/2003 | Lindgren et al. |
| 6,762,429 B2 | 7/2004 | Aonuma |
| 6,798,217 B2 | 9/2004 | Scheible |
| 6,861,954 B2 | 3/2005 | Levin |
| 7,030,772 B1 | 4/2006 | Lee et al. |
| 7,090,395 B2 | 8/2006 | Glazer |
| 7,194,064 B2 | 3/2007 | Razzano et al. |
| 7,216,054 B1 | 5/2007 | Pchelnikov et al. |
| 7,319,396 B2 | 1/2008 | Homanfar et al. |
| 7,518,518 B2 * | 4/2009 | Homanfar et al. ........ 340/572.1 |
| 7,605,688 B1 * | 10/2009 | Seah ..................... 340/572.1 |
| 2004/0008123 A1 | 1/2004 | Carrender et al. |

FOREIGN PATENT DOCUMENTS

| | | |
|---|---|---|
| EP | 1374791 A1 | 1/2004 |
| JP | 62071198 | 1/1987 |
| WO | 00/38570 A1 | 7/2000 |

* cited by examiner

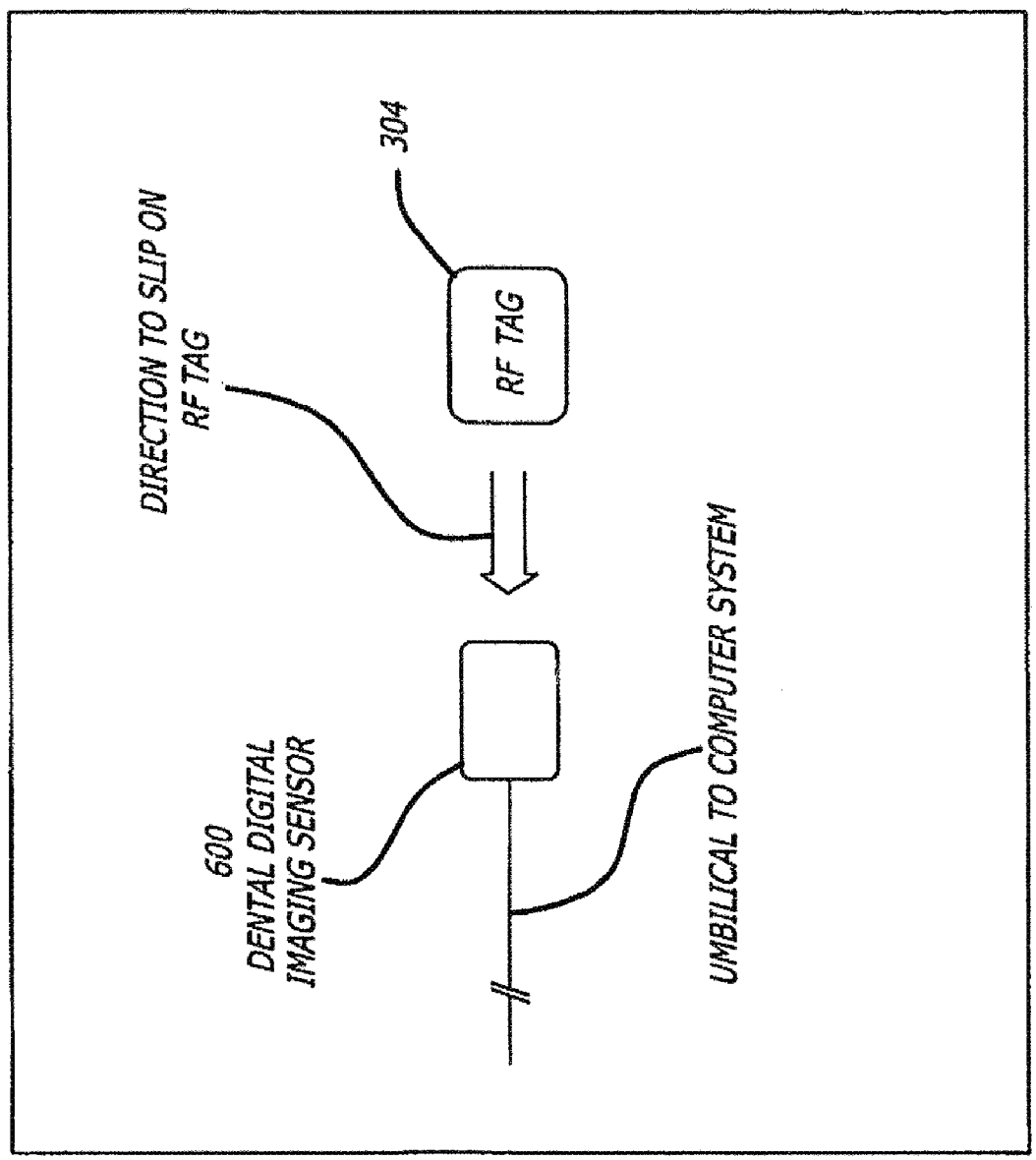

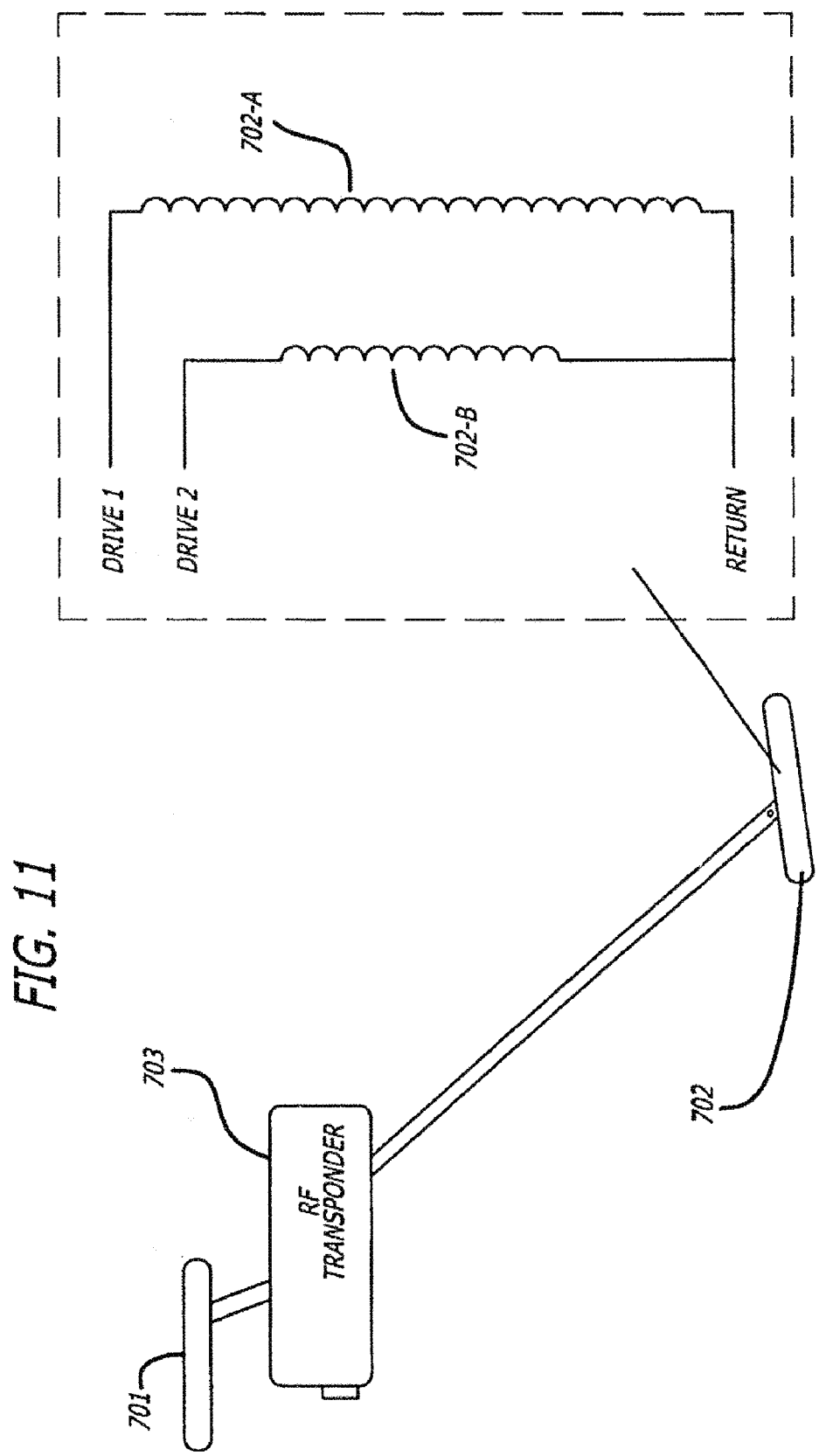

RFID TRANSDUCER ALIGNMENT SYSTEM

CROSS-REFERENCES TO RELATED APPLICATIONS

This application is a continuation of U.S. patent application Ser. No. 11/959,249, filed Dec. 18, 2007, issued as U.S. Pat. No. 7,518,518; which is a continuation of U.S. patent application Ser. No. 11/205,348, filed Aug. 16, 2005, issued as U.S. Pat. No. 7,319,396. This application also claims the benefit of U.S. Provisional Application Ser. No. 60/602,223, filed Aug. 16, 2004 and U.S. Provisional Application Ser. No. 60/602,751, filed Aug. 18, 2004, the contents of which are hereby incorporated herein by reference.

BACKGROUND

1. Technical Field

This disclosure relates generally to providing enhanced functionality for common radio frequency identification (RFID) technologies and devices, and more specifically to the detection of radio frequency (RF) component alignment, for example, an x-ray critical-alignment apparatus.

2. Description of the Related Art

The general function of a given RFID transponder or "tag" is to act as a "remote sensor device" for a given RF interrogator. When enabled, an RF interrogator's carrier transmit/data receive coil produces an electromagnetic field of flux at a predetermined frequency, which creates a radiated "carrier" transmit signal. When such an RFID tag is placed in close proximity to an RF interrogator, the RFID tag "powers up." Accordingly, the activated RFID tag is impressed with the carrier transmit signal, and in response certain passive electronic components of the RFID tag begin to self-oscillate, which creates a secondary electromagnetic (EM) field of flux at a predetermined frequency within and about the RFID tag. After the RFID tag is activated and when the received carrier transmit signal is of predetermined ideal amplitude, as set by predefined design criteria of the RFID tag and firmware thereof, the RFID tag begins to transmit a serial data stream of "canned/stored" information. Data transmission is generally accomplished by means of the RFID tag shunting its carrier-receive/data transmit coil or antenna, according to the RFID tag's design and predefined data protocol, etc.

When an RFID tag begins to oscillate so as to radiate a specific RF signal and electromagnetic field of flux, the RF interrogator carrier-transmit coil becomes impressed with the RFID tag's "return" RF signal. The impressed return RF signal upon the RF interrogator carrier-transmit coil is commonly referred to as "backscatter" or a backscatter signal. The backscatter signal generally alters certain characteristics of the RF interrogator carrier-transmit signal. Such carrier-transmit signal alterations, even as they might be minute initially, can be detected by appropriate RF interrogator front-end circuitry. When actual RFID tag serial data stream transmission occurs, the RF interrogator acts to detect the back-scatter signal, generally through the use of an "envelope detector" circuit. The RF interrogator will then condition/filter and amplify the backscatter signal to obtain a resultant "clean" data stream signal. Thereafter, the RF interrogator's microcontroller may "test/decode/read" and be configured to respond to the resultant signal, for example, by inputting a product name, code, and price into a cash register when an item containing an RFID tag is scanned, or by setting off an alarm when someone walks out of a store without purchasing an item containing an RFID tag. However, current RFID technology has been limited to its namesake: product "identification." Thus, the technology has not been applied in alternatively new ways or with regard to differing applications. Accordingly, RFID technology has not been applied to sensor "alignment" functionality, such as for an indication of best alignment of non-contact x-ray film positioning.

During the common and standard process of taking dental x-rays, special tools and several tedious steps are often required. Two options for taking x-rays are known wherein: 1) a molded x-ray film holder, which generally has sharp edges around its periphery, is loaded with an x-ray film and together is placed in a patient's mouth to bite down on (which is most discomforting for most patients due to the sharp edges), such that a dental technician or doctor must then visually estimate the position of the film holder so as to take an x-ray; or, 2) wherein a molded x-ray film holder, also having sharp edges around its periphery, is loaded with an x-ray film and together is placed onto a "rim holder" device (a long bar, generally of metal, with an x-ray film holder receiving device at one end, and an x-ray head apparatus receiving device at the other end), which is then collectively placed in a patient's mouth to bite down on (which is extremely discomforting for most patients due to the sharp edges, as well as due to the bulkiness of the rim holder apparatus) with only the x-ray head apparatus receiving device protruding from the patient's mouth such that a dental technician or dentist would then place the x-ray head into the x-ray receiving device so as to take an x-ray radiograph.

Aside of the general need for special alignment tools, the disadvantages of the above two options are several: 1) often additional x-rays are required to be taken because of improper alignment of the x-ray head apparatus to the x-ray film, especially when the location/position of the x-ray film is manually estimated, and often, when; 2) the rim holder is improperly located/positioned in a given patient's mouth, which creates; 3) loss of both time and expense, and, which additionally; 4) exacerbates a given patient's discomfort. The present disclosure was devised to overcome these challenges. The first concept considered was to provide a system that might permanently eliminate the need for a rim holder device/alignment tool. The second concept considered was to alter the design of the common x-ray film holder device so as to eliminate its sharp edges. The third concept was to identify a system by which the taking of dental x-rays would become less intrusive, yet more accurate.

The basis for RFID technology appears to offer the most ideal solution to the current problems with dental x-rays. Heretofore, RFID technology in practice and application has mostly been used for product and other commodity "identification" purposes. Apparently, such technology had not been used for exacting a critical alignment of an x-ray head apparatus to an (often hidden) x-ray film. One aspect unknown in the art was a system that would permit attachment of a predetermined RF tag in proximity of an apparatus and that would incorporate those components required for building a customary RF tag device. Such a system was lacking in newer technology apparatus (for example, digital radiography) and in well-known technology apparatus, such as dental x-ray film holder devices. Thus, a new RF tag architecture and device is required. However, digital radiography, in terms of equipment and supplies, is extremely expensive, and as it relates to practicing dentists remains of price and expense that is currently highly prohibitive to manifold dentists. Therefore, a great many dentists, especially in rural-type environments, still make use of the established technology such that the dentists are still using both x-ray film and x-ray film holder devices.

Another aspect unknown in the art is an electronics design that would act as an RF interrogator and that would have a remote yet attached "transmit/tag sense/antenna" coil. Such a coil, which transmits a carrier frequency to enable the new RF tag device and that also acts to receive data from the enabled new RF tag device, would need to be devised so as to fit upon or mechanically interface to the active end of a given dental x-ray head apparatus.

One issue in creating a dental-oriented non-contact RF transducer system is that a given dental RF tag must be physically smaller than the accompanying dental RF carrier transmit/data receive coil. In fact, to meet the criteria for obtaining a "best-alignment" scenario with regard to most RF-based transducer alignment systems, a given RF tag thereof, and particularly its RF carrier receive/data transmit coil, must generally remain smaller than the system's associative RF carrier transmit/data receive coil. Another issue to operational practicality for a dental application is that "non-contact" operation be obtained, wherein a given x-ray head apparatus would never (intentionally or need to be caused to) touch a patient's face, especially in the course of alignment of the x-ray head apparatus to the dental RF tag within a patient's mouth. This issue is not in the least trivial since known RFID technology did not allow for spacious RF sensor/tag distance sensing, particularly in wholly scaled-down RFID systems. Various common RF tags currently available were used in test beds, and were found to be grossly lacking as it concerned desired operational distance to a similarly available RF interrogator.

It was found that when an RF tag was placed in a patient's mouth and behind the teeth (as would normally occur in a dentist's office), then valid sensing-distance was no more than one inch, and often much less. The RF interrogators carrier transmit/data receive coil needed to be placed inward on, at or extremely close to the cheek in order to "read" a common RF tag. Thus, commonly available systems were both non-ideal and impractical for a dental x-ray application. Therefore, there is a need for an enhanced RF interrogator analog "front-end" circuit having additional features.

As will be appreciated by those of skill in the art, providing a dental x-ray RFID positioning system incurs several design challenges, including: 1) dental RF tag size, which being rather small, produces only a small RF field of flux at resonance; 2) sensing distance to a given RF tag of at least two inches is desirable; 3) dental RF interrogator carrier transmit/data receive coil size, which also being rather small, has a limited range for detecting a remotely radiated RF signal from an RF tag when an RF tag is activated; 4) data stream signals received by the dental RF interrogator carrier transmit/data receive coil are in the microvolt range when the RF tag is several inches away; 5) such signals, when then fed into operational amplifier circuits, generally can not be distinguished or easily separated from base-noise levels of operational amplifier circuits, and thus, 6) the resultant signal from the operational amplifier circuits contains both inherent and free-air radiated noise, as well as the desired data signals RF carrier transmission components, making "valid" signal detection difficult; and 7) even with filtering, free-air radiated alternating current (A.C.) signals are amplified and become part of the net/final signal structure from the operational amplifier circuits, thereby, grossly affecting the final signal integrity, particularly when obtained by a highly sensitive RF interrogator analog front-end circuit.

Thus, what is needed and heretofore unknown is an RF transducer non-contact alignment system that fulfills dental x-ray application requirements, that solves these identified technical challenges, and that provides a fully operational product. There is also a need for RFID-type technology operable over greater distances between certain types of RF tags and interrogators. There is also a need to fill the technological gaps and voids in the practical applications of RFID technology. There is a further need for critical RF tag/sensor alignment functionality to establish new applications within the RFID industry, especially for critical RF tag alignment.

BRIEF SUMMARY

The present disclosure is directed to a new application for RFID technology that will enhance the industry as a whole. The RFID system of the present disclosure utilizes certain design methodologies so as to provide inexpensive and uncomplicated apparatus for detecting RFID tag-to-RFID interrogator alignment.

The present disclosure provides a simple, functionally enhanced, and new RFID system concept, wherein presently available RFID systems have an opportunity to be improved upon or expanded by various new features and functionalities, including the capacity to detect the parameter of "alignment." The present disclosure further provides a new type of RF interrogator specifically designed for the dental industry, medical imaging systems, and other such industries for use with digital radiography. The present disclosure also provides a new RFID system having a new type of RF tag device and x-ray film holder. The RF tag device and x-ray film holder may allow presently utilized dental x-ray films to be placed into a re-devised, intelligent, and more comfortable (for the patient) film holder. The RF tag device and x-ray film holder may be applied to contemporary "digital x-ray imaging sensors" by allowing contemporary digital x-ray imaging sensors to be critically aligned to a given dental x-ray machine head/gun apparatus, rendering repeat imaging unnecessary.

The present disclosure also provides a new RFID system, wherein dental x-rays may be taken with great accuracy resulting from the ability to denote critical alignment of a digital x-ray imaging sensor and/or dental x-ray film in a patient's mouth. The system of the present disclosure may be configured to denote critical alignment of a digital x-ray imaging sensor or dental x-ray film holder within a patient's mouth without the need for commonly used special tools, procedures or devices. The RFID system may be configured to store patient and other information in the RF tag device or x-ray film holder or both.

The present disclosure includes a new RFID system utilizing x-rays and other radiography imaging so as to provide an automatic RF tag seeking mode of operation. For example, a given x-ray head apparatus may be configured to move on its own accord. When enabled, the x-ray head apparatus may locate a (perhaps) hidden RF tag device, such as during a dental application, and ultimately align itself to a given located RF tag device. The x-ray head apparatus may be further configured to automatically obtain a desired x-ray image and store certain data. The x-ray head apparatus may be further configured so that the device cannot activate and provide a radiograph until alignment to a given RF tag device has occurred. Such a system provides a new safety mechanism against impromptu enabling of the x-ray machine apparatus and may render repeat imaging unnecessary.

The present disclosure improves upon the present designs of certain RFID interrogator devices by providing for one or a multiplicity of RF interrogator carrier transmit/data receive coils, depending on the application or the need. One or a multiplicity of RF interrogator carrier transmit/data receive coils may be provided in a given system, depending on the application or the need, each resonant to the same or differing frequencies. In a multiple coil system, and depending on the application, the size of the RF interrogator carrier transmit/data receive coils may vary. Further, the multiplicity of RF interrogator carrier transmit/data receive coils may be fixed about a given RF interrogator enclosure, or placed remote from the RF interrogator by using one or more appropriate cable devices.

The present disclosure provides for improving upon the present designs of certain RFID interrogator devices for use with hand-held fixed-in-place, stationary and permanently mounted applications. Such hand-held, fixed-in-place and similar applications may be independent of an applied power source, for example, an alternating current (A.C.) wall socket or a direct current (D.C.) battery.

The present disclosure improves upon the present designs of certain RFID interrogator devices by providing a system for indication of the detection and presence of a given RF tag by a given RF interrogator by various devices and circuits, including either or both: audio or visual techniques and apparatus. The system provides for indication, within predefined limits, of the distance from a given RF interrogator's carrier transmit/data receive coil to a given detected RF tag by various devices and circuits, including either or both audio or visual techniques and apparatus. The system also provides for indication of the detection of valid data from a given detected RF tag by a given RF interrogator by various devices and circuits, including either or both audio or visual techniques and apparatus.

The present disclosure improves upon the present designs of certain RFID devices by providing a system for indication of critical alignment of a given detected RF tag by a given RF interrogator by various devices and circuits, including either or both audio or visual techniques and apparatus. The system may provide indication of a given RF interrogator's status, such as "elapsed warm-up time," or "ready for operation," for example, from various devices and circuits such as from audio or visual techniques and apparatus. The system may also provide for indication of a given RF interrogator's carrier transmit frequency or frequencies from such devices, circuits, and techniques. The system may also provide for varying and indication of a given RF interrogator's carrier transmit frequency or frequencies. Further, the system provides for tuning/detuning and indication of a given RF interrogator's carrier transmit frequency or frequencies by various devices and circuits, including either or both audio or visual techniques and/or apparatus.

The present disclosure improves upon the current designs of certain RFID interrogator devices by providing a system for selection and indication of a given RF interrogator's explicit carrier transmit drive signal waveform or waveforms by various devices and circuits, including either or both audio and visual techniques and apparatus. The system may also provide for indication of a given RF interrogator's carrier transmit amplitude or amplitudes by such devices, circuits, and techniques. The system may further provide for indication of the presence of a given RF interrogator's carrier transmit signal or signals from such devices, circuits, and techniques. The system also may provide for indication of the presence of a given RF interrogator's carrier transmit/data receive coil or coils. Further, the system may provide for selection, as well as the indication of selection, of one or more carrier transmit/data receive coils attached to a given RF interrogator. Also, the system may provide for the indication of the current mode of operation of a given RF interrogator (such as idle or seek mode) by various devices and circuits, including either or both audio or visual techniques and apparatus.

The present disclosure improves upon the current designs of certain RFID interrogator devices by providing a system for on-the-fly or in-situ RF tag programming and the indication of the same by various devices and circuits, including either or both audio or visual techniques and apparatus. The system may provide for sensing the parameter of critical alignment in a fixed or variable three-dimensional space and indication of the same by such devices, circuits, and techniques. The system may further provide for audio feedback for a user in the course of operation, whether in the form of tones or voice by various devices and circuits. Further, the system may provide for audio feedback for a user in the course of operation, whether in the form of tones or voice, wherein pitch and/or volume, or expression, or such that, might be altered by a given RF interrogator's response to certain sensed parameters, input, or by such various devices and circuits.

The present disclosure improves upon the current designs of certain RFID interrogator devices by providing a system having a user keyboard of some nature, whereby a user may, for example, input or set or define certain data or criteria, or retrieve information and other data from or to various devices and circuits. The system may also be configured with one or more display apparatus, primarily for user feedback, whether it or they be LED or LCD, or the like, in nature or a mixture thereof. The system may provide for at least one external communications port. Such an external communications port may accommodate a transmission or data link to and with a computer or a printer or both. Further, the system may provide for remote placement of certain visual indicators or audio devices near or at a given RF interrogator carrier transmit/data receive coil or upon an RF interrogator.

The present disclosure improves upon the present designs and functionality of RFID interrogator devices and systems and their components by providing not only for RF tag or sensor detection and reading, and sorting, or other functions as pertinent to a given application, but for explicitly programming a given RF tag or sensor device by various devices and circuits.

The present disclosure includes a method for constructing an RF tag envelope from a rubber, plastic, vinyl, or other suitable material so as to allow for dental x-ray film insertion or digital x-ray imaging sensor attachment. The RF tag envelope containing an electronics circuit may also be constructed from such materials so as to allow for dental x-ray film insertion or digital x-ray imaging sensor attachment. Such an RF tag envelope may be fabricated so as to allow for dental x-ray film insertion or digital x-ray imaging sensor attachment that the electronic circuit may be minimally comprised of a coil apparatus, a capacitor device, a power conditioning circuit and a microcontroller circuit device.

The present disclosure further includes a method for constructing and fabricating an RF interrogator envelope from rubber, plastic, vinyl, metal, or other suitable material. The RF interrogator envelope may include a printed circuit board apparatus and whereon various and sundry electronic components may be attached. The electronic components on the circuit boarding include certain discrete analog and digital electronic devices, passive electronic devices, a microcontroller circuit device and visual display and audio devices. The circuit board may also include or have attached one or more connectors, including that of an applied power source connector.

The present disclosure also includes a method for constructing and fabricating an RF envelope from plastic, vinyl, or other suitable material for use with a dental x-ray machine head or gun apparatus attachment, such as insertion. The RF antenna envelope may be fabricated so that a dental x-ray machine head or gun apparatus is attached or inserted on one end, and a coil apparatus may be attached to the opposite end of the envelope. Such an RF antenna envelope may be configured so that visual or audio indicator devices and one or more connector devices may be attached to the envelope. Such connector devices may attach to one or more cable apparatus so that the RF antenna envelope may ultimately be attached to the RF interrogator envelope.

The present disclosure includes a method for constructing and fabricating an RF tag envelope from plastic, vinyl or other suitable material. The RF tag envelope may be configured with various and sundry electronic components having discrete analog and digital electronic devices, passive electronic devices or microcontroller circuit devices so as to construct an RF tag device. Such an RF tag device may be configured for attachment about a digital radiography apparatus or in synchronicity with customary x-ray imaging apparatus, for example, x-ray film requiring an x-ray film holder.

The present disclosure further includes a method for utilizing an RF tag device, RF antenna device, and an RF interrogator device, each in a completely assembled form, wherein each component is configured to work in synchronicity with each other component. The components may be further configured together and collectively to form and operate as an RFID transducer apparatus and system. Such an RFID transducer apparatus and system may function and be used as a non-contact "alignment" apparatus or tool. In certain applications the RFID transducer apparatus and system may perform more basically as an enhanced RFID system.

BRIEF DESCRIPTION OF THE SEVERAL VIEWS OF THE DRAWINGS

Other features and advantages of the disclosure will become apparent from the following detailed description, taken in conjunction with the accompanying drawings, which illustrate, by way of example, the features of the disclosure.

FIG. 10 is a schematic representation of an alternate embodiment of an RF transducer alignment system of the present disclosure illustrating a dental digital x-ray imaging sensor and an RF tag device.

FIG. 11 is a schematic representation of an alternate embodiment of an RF transducer alignment system of the present disclosure illustrating a multi-form RF antenna.

DETAILED DESCRIPTION

Figure 1:
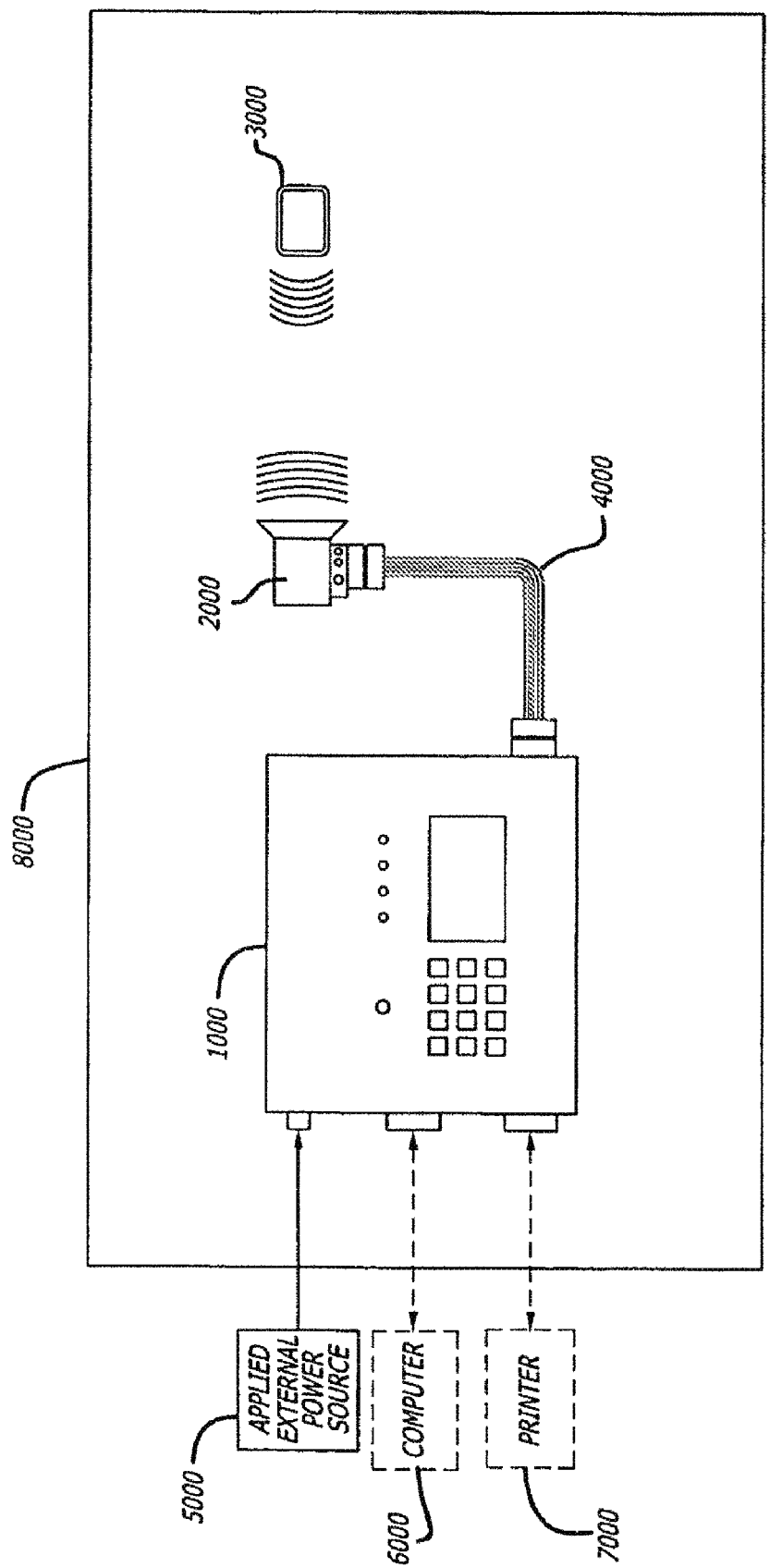
FIG. 1 depicts a system diagram of an embodiment of an RFID transducer alignment system generally devised for dental applications according to the present disclosure.

As shown in the drawings for purposes of illustration, the present disclosure is directed to a beneficial and novel electronic design, the basis of which is founded on RFID (radio frequency identification) technology. The present disclosure provides an altogether new RFID application having enhanced levels of utility and practical functionality over present-day common or standard uses of the RFID technology. This RFID system is beneficially applicable to those apparatus or products that require or might make use of non-contact power control or operation, non-contact accessibility or enabling, and non-contact entry. The disclosure is also useful for those products, apparatus, or devices that require or might make use of non-contact object or target sensing or detection, intelligent non-contact sensor response systems, and non-contact object or target data programming and data retrieval. The disclosure may also be applied to systems requiring non-contact alignment capability, for example, dental and medical x-ray and imaging technologies. In addition, the disclosure is relevant to non-contact detection, monitoring, control or feedback for the specific alignment of certain systems and components of systems that would be enhanced by a remote alignment or positioning capability.

The system of the present disclosure is particularly applicable in the activity of proper positioning of a given x-ray machine "gun" or "head" apparatus to a given x-ray film apparatus. The system utilizes a simple non-contact alignment procedure without the need for implementing "customary" alignment devices or techniques. The system is applicable to newer technology (for example, digital radiography) and to established technologies, such as x-ray film and x-ray holder devices. As a function of operation, the present disclosure has the capacity to be utilized in many applications, wherein, and broadly speaking, an "RF tag" device (minimally composed of a carrier-receive/data-transmit coil, a resonance capacitor, a power conditioning circuit, a microcontroller, and a coil shunting circuit) acts as a "remote target/sensor" or "system activation key." The RF tag is configured to interface with an "RF interrogator" device, minimally composed of a carrier-transmit/data-receive coil, a resonance capacitor, a carrier signal drive circuit, an applied data-receive signal detection circuit, various applied data-receive signal filters, various applied data-receive signal amplifier circuits, and various logic devices or a microcontroller wherein the RF tag and RF interrogator, together, create a non-contact RF transducer alignment function and system. The system is configured such that when the RF interrogator is in the near presence of the RF tag, then the RF interrogator ultimately causes to occur one or more predefined actions or activities. Such actions may be determined by the real-world function(s) desired, application, and the type of end-user product manufactured.

The present disclosure provides for a non-contact RF transducer system minimally composed of at least one RF tag device and a control electronics package, such as an RF interrogator. Together, the RF tag and RF interrogator act to minimally perform as other RFID systems, yet may also provide for an RF transducer a non-contact "alignment" system. The RFID system of the present disclosure may be adapted for use as an intelligent "item or device detector," an electronic non-contact pass-key system, a medical history bracelet antenna system, a computer enable apparatus, and a keyless car door and trunk opening system, as examples. As may be appreciated by those of ordinary skill in the art, many other applications for non-contact RFID sensor alignment exist that may benefit from a system configured to detect, monitor, and respond to the particular alignment of one apparatus to another. Such applications include when space docking one vehicle or platform to another, locating the internal communications port on a marine environmental transducer so data can be recovered from the transducer without opening its enclosure or using an external connector, and for use in exactingly monitoring the positioning of various hatches or flight-control surfaces, etc., on commercial aircraft.

Numerous hand-held applications are apparent, for example, exactingly identifying the position of in-wall, underground or buried cabling or gas pipes, and the like, wherein homeowners and utility personnel could easily denote not only the "where" and "what" of what lies hidden from view, but perhaps, when installed or how deep, by using one or more concealed RF tag devices. Another hand-held application includes a luggage identification system, wherein ticket handlers may cause the programming and attachment of an RF tag to luggage. The benefit of such a system includes far more accurate and simple destination processing, and may also include insuring the rightful owner during baggage "pickup" should a question arise.

One benefit of the present disclosure is demonstrated when an RF tag is placed behind a given non-transparent material, and so not normally visible to a user/operator of the present disclosure, the user/operator may utilize the RF interrogator to locate the RF tag (or vice versa). The RFID system may be used to locate the hidden RF tag and to also easily identify a "best-alignment" (of the RF tag to the RF interrogator) scenario as well, if the latter is desired. In essence then, the RF interrogator is, or may be, intended to identify the best position of, or "line-of-sight" of the RF tag to the RF interrogator for then performing certain predefined activities. In some instances, the RF tag may or may not actually be hidden from view of the user/operator. Thus, if alignment of the RF tag to the RF interrogator is required, and if the alignment procedure is left solely to a human, wherein one might use a best guess or estimation process, and if the alignment is considered critical, then errors can occur in the attempt for alignment, providing the processes generally insure a "best-alignment" scenario fails to occur.

The potential disadvantages of humanly performed alignment activities are overcome by the present disclosure, in that the present disclosure and RF interrogator component thereof automatically identifies a "best-alignment" scenario for a user/operator. In other applications, exacting alignment between the RF tag and RF interrogator may at times not be critical, and that simple RF tag detection is all that is required. In other applications, perhaps utilizing a hand-held RF interrogator unit, retrieving certain data a perhaps hidden RF tag may be keenly desired when the hand-held RF interrogator is within "reading" distance of a given RF tag. In many such instances, less than perfect alignment between a given RF tag and an RF interrogator is wholly acceptable and practical, as the present disclosure can easily allow for non-critical RF tag alignment detection and readings.

Another example of an application of the system of the present disclosure includes locating and identifying hidden control knobs or valves and/or buried coupling devices. Such an application requires exacting location of such devices in order that one may accurately unveil the devices' physical view before servicing or repairing or upgrading may be accomplished.

The present disclosure and its two main components (an RF tag device, and an RF interrogator device) provide for one or more embodiments of the RF tag device. The RF tag remains minimally composed of: 1) an LC tank circuit, having at least one carrier signal receive/data transmit coil of a predetermined value; 2) a resonant capacitor of a predetermined value to work in parallel with the carrier signal receive/data transmit coil, wherein both collectively act in response to a predefined applied carrier signal, so as to be caused to resonate with the applied transmit carrier signal; 3) a power conditioning circuit, wherein a portion of the resonant energy generated by the LC tank circuit is used to create the required operating power for; 4) an on-board microcontroller device, wherein the microcontroller device can be configured to identify certain of the RF tag's operational parameters, and whereby a predetermined serial data stream may be generated from a predetermined protocol by using; 5) a carrier signal receive/data transmit coil shunting circuit; or 6) an LC tank circuit shunting circuit. As may be appreciated by those skilled in the art, present technology provides that an RF tag device does not require a battery for operation, but instead remains responsive to a near or close proximity externally applied carrier signal and of a frequency that is conducive to cause resonance of a given RF tag's LC tank circuit.

The RF interrogator may be a wall powered or battery operated device. The present disclosure provides for one or more embodiments of the RF interrogator device, wherein the RF interrogator remains minimally composed of: 1) an LC tank circuit, composed of at least one carrier signal transmit/data receive coil of a predetermined value; and 2) a resonant capacitor of a predetermined value to work in parallel with the carrier signal transmit/data receive coil, wherein both collectively act in resonance to create a predefined applied carrier signal; when 3) a predetermined carrier drive signal is applied thereto; 4) an RF tag signal-detection circuit, the obtained signal of which is applied to; 5) predetermined filters and amplifier circuits, the resultant signal of which is then applied to; 6) a microcontroller device configured or programmed for desired operations and functions, as well as the ability to read the serial data transmitted by a given RF tag, whereby; 7) the microcontroller may cause to occur certain predetermined real-world activities, predicated on its associated predetermined firmware and input/output (I/O) circuitry and specific application or need.

Another aspect of the system of the present disclosure is to provide for remote placement of the interrogator carrier signal transmit/data receive coil from the RF interrogator electronics package, thereby providing a third main component of the system. Such a feature accommodates more easily the placement of the RF interrogator coil (hereinafter referred to as "RF antenna" or RF antenna device) in a given "work area." This aspect may be accomplished through the attachment of a pre-configured cable between the RF interrogator electronics package and its associated carrier transmit/data receive coil or RF antenna. The system also provides for detecting and displaying the distance, within certain predefined limits, of the RF tag to the RF interrogator carrier transmit/data receive coil. The system further provides the user with a visual indication of when the RF interrogator detects the RF tag. Such detection can act to wake a "sleeping" RF interrogator microcontroller or wake an RF interrogator microcontroller that resides in "idle" mode. This feature also provides feedback to the user/operator that an RF tag detection has occurred. The visual indication is perhaps best accomplished with an LED (light emitting diode), particularly in terms of indicator life longevity and vibration resistance. The system may also provide the user with a separate visual indication of when the RF interrogator detects a readable or valid data stream from a given RF tag. Predicated on data protocol and other data-form factors, such detection can act to cause an RF interrogator microcontroller to ascertain the RF tag data stream to be valid and, thus, reliably useable. This feature also provides feedback to the user/operator that a given RF tag "reading" by the RF interrogator may be in process.

It is also a function of the present disclosure to provide for those instances wherein one or more audio tones are desirable or required. An audio tone generator may provide additional feedback to the user/operator that tag detection or reading has occurred, for example, without need for the user/operator to look away from where or what he or she is presently (visually) focused on. The audio tone generator may simply provide for singular tone structures, or may provide pitch/frequency or volume changes (predicated, for example, on RF tag distance) and may offer voice feedback or commands. The system may also provide for RF tag detection with valid RF tag datastream visual indicators and for an audio speaker device at or in close proximity to the RF interrogator carrier transmit/data receive coil.

The system of the present disclosure may further be configured with a display device, such as a liquid crystal or OLED display. Such a display device may act to provide a user/operator with such predefined details as instructions, captured RF tag information, and other operational information. The system may be further configured to allow an RF interrogator to interface with a computer and printer so as to remotely capture, display, and record some or all the information in a given RF tag.

The system of the present disclosure may be configured to provide for variable RF carrier transmit signal frequency control so as to utilize various RF tags by various manufacturers, having varying frequencies of resonance. Variation of the RF carrier transmit signal frequency can be implemented with an adjustment potentiometer or by a keyboard entry. Other mechanisms may be used, such as the switching in and out of various resonance capacitors by altering the divide-by rate of certain logic devices, by a tunable coil device, or a combination thereof.

In addition, the system of the present disclosure may be configured to visually or audibly indicate when power has been applied to the RF interrogator. Similarly, the system may visually or audibly indicate when a predefined warm-up period has elapsed and system stability has occurred. Such a feature is perhaps most desirable when a given electronics circuit utilizes a clock or oscillator circuit.

The system of the present disclosure may also visually or audibly, or both, indicate maximum (or even perhaps, less than maximum) carrier transmit signal strength or amplitude. The system may further allow for displaying the carrier transmit signal frequency, whether based upon an LED array or by using an alphanumeric or graphics display of some nature. In addition, the system may be configured with various mechanisms to provide for indication of the presence of the carrier transmit signal and to provide for indication of the presence of the carrier transmit/data receive coil.

Further, the system of the present disclosure may provide selectable carrier transmit drive signal waveform control. The carrier transmit drive signal control may allow for the use of sine triangular or square waves, pulse width modulation or other signal waveform structures. The system may be configured to provide for carrier transmit drive signal frequency tuning and detuning control circuitry. Predicated on the nature of a given carrier transmit drive signal waveform and its potential harmonics, the system may allow signal tuning and detuning so as to achieve a "best-case" resonant waveform.

Another aspect of the system of the present disclosure is to provide for on-the-fly and in-situ programming of a given RF tag. One such application is wherein a dentist utilizes the system of the present disclosure to take a molar x-ray. Accordingly, the customary "rim holder" (used to both hold the x-ray film and assist in x-ray head alignment) may be replaced with an intelligent mouth x-ray film RF tag device. The system may be configured such that the dentist's RF interrogator to identify a "best-alignment" for taking an x-ray. As the dentist's RF interrogator indicates a valid "read" of the RF tag (before or after the RF tag has been placed in the patient's mouth), the dentist could type in certain information on a keyboard of which he or she wishes to be programmed into the intelligent mouth x-ray film RF tag device, such as a patient's name, date, and/or client number. That particular x-ray film RF tag may remain permanently programmed and be directly traceable to that patient.

The system of the present disclosure may have other features, such as to indicate whether a given RF interrogator is in a particular mode of operation, for example, data programming mode, tag detection or alignment mode, or idle mode. Other features of the system may include: 1) the capability of the RF interrogator circuitry to provide indication of "best-alignment" without the need for utilizing customary alignment tools, devices, or procedures; and 2) to do so in a non-contact manner, as in the above dental example where two net benefits and results are: a) less complication for the dentist; and b) an enhanced comfort factor for dental patients.

Additional embodiments of the system of the present disclosure can be constructed such that the system may allow for those applications wherein a particular location must be reliably identified in three-dimensional space. For example, three RF tags may be used in an "x", "y" and "z" axis configuration that are configured to interface with a triple-coil RF interrogator device also configured for "x", "y" and "z" axes. Further, the "x", "y" and "z" axes may or may not be relative to the predetermined positioning of the triple-coil RF interrogator device or the predetermined positioning of the three RF tags. Such a system may be beneficial if the "x", "y" and "z" axes of the RF tags or RF interrogator (or both) are required to be absolute or are allowed to reside at non-absolute angles/attitudes in free space. In this manner, the "x", "y" and "z" axes for either the RF tags or the triple-coil RF interrogator may be utilized as fixed or variable. If one or the other components of the system (the RF tag or RF interrogator, or both) are desired as variable, then the system offers significant repositionability and can be variably indexed about a full 360 degree locus. Accordingly, three RF tags and three RF interrogators could be employed so as to work as a single collective transducer apparatus or employed so as to function as three independently positionable transducer apparatus-sets. Each transducer apparatus-set may be configured to be positioned upon a separate predetermined or variable axis or plane. Alternatively, a single RF interrogator device could be used, wherein it remains configured to utilize three carrier transmit/data receive coils of the same or differing sizes and carrier frequencies. Where this 3-D function is used with various imaging technologies (for example, radiation treatments and laser surgery) medical equipment alignment and/or procedural site loci, identification is important to both doctor and patient.

Furthermore, the system of the present disclosure may be configured with the capacity to allow for exacting data programming of the RF tags for simple or specific utility, for example, patient processing. The programming may allow for such information as patient identification, allergy or medication warnings, past medical history, reason for admittance, date of admittance, procedure(s) to be performed, patient name, as well as patient age, date of birth, diet type, debilities, etc.

Additionally, the system of the present disclosure can be constructed in various sizes and with various features. Alternative embodiments of the system can be configured such that the system may address such applications as latch-key kids and intelligent door lock systems (eliminating the need for physical keys); gardening/plant/crop/tree I.D. markers (which might also provide for feeding and care instructions); personal medication allergy warning bracelets; patient medical history or processing tags; product history tags (with particular utility as regards warranty-period initialization or product tracking); newborn tracking and I.D. tags (which can assist in eliminating "swapped" newborn errors, as well as provide for accurate caretaker/parent access, or the setting off of alarms when an attempt to otherwise hold or remove a child has occurred); land boundary or corner markers (particularly useful with regards to certain mining "claims"); pet access tags (allowing a pet access to or from a home or yard at particular times of day, as an example); vehicle and vehicle compartment entry systems; computer access systems; traveler luggage control and management systems; utility, gas, and water line detection systems; ballpark, entertainment, and transit pass systems; medical diagnosis, imaging, and radiation systems; laser surgery systems; and of course, all manner of x-ray systems, to mention a few. Given such potential real-world applications, it is therefore the intended purpose of the present disclosure to offer a new, uncomplicated, utilitarian, reliable, and inexpensive yet intelligent and precise means of non-contact sensor alignment as pertains to RF tag devices and RF interrogator devices, which herein together, now provide for a novel RFID transducer system for critical-alignment as regards x-ray and medical applications, as well as those myriad applications wherein the issue of "alignment" is not a critical one.

Referring now to FIG. 1 and item 8000 in particular, the figure represents a physical system block diagram of an embodiment of an RFID transducer alignment system providing for an altogether new RFID application and market, and, the general enhancement of common RFID systems according to the present disclosure.

Referencing FIG. 1, item 1000, referred to herein as "RF interrogator" and "RF interrogator means," is an assembly caused to be attached to item 2000, referred to herein as "RF antenna" and "RF antenna means," by means of a predetermined cable apparatus, item 4000, referred to herein as "antenna umbilical cable" and "antenna umbilical cable means." Item 3000, referred to herein as "RF tag" and "RF tag means", remains the final subsystem component of the RFID transducer alignment system but is in no way attached to any other component of or within the system.

Generally speaking, when items: 1000 (the RF interrogator), 2000 (the RF antenna) and 4000 (the antenna umbilical cable) have been assembled, and when item 1000 (the RF interrogator) is then enabled, by means of a predetermined power switch and applied power source, item 2000 (the RF antenna) will predeterminedly begin RF emissions, and at a predetermined frequency, of 100 kilohertz or greater, resulting in a radiated RF field of flux from item 2000 (the RF antenna).

When the RF tag 3000, also constructed to oscillate at a predetermined frequency of 100 kilohertz or greater, and which frequency is ultimately caused to be near or identical to that of the RF antenna 2000, and when brought within a predetermined distance of the RF antenna 2000, the RF emissions of the RF antenna 2000 will cause the LC tank circuit of the RF tag 3000 (more fully depicted in FIG. 4), to begin to self-oscillate.

As the LC tank circuit of the RF tag 3000 begins to self-oscillate, internal power for the RF tag 3000, is created by an internal power conditioning circuit, and ultimately, a serialized data stream is generated by an associated and integral microcontroller device. The serialized data stream is applied to the LC tank circuit, which then provides the effect of dampening the oscillations of the RF tag coil.

Therefore, and as the LC tank circuit of the RF tag 3000 begins to self-oscillate, RF emissions are predeterminedly created therefrom, which can be observed to be impressed with serialized data from the associated and integral microcontroller device means. In essence then, the RF emissions from the LC tank circuit of the RF tag 3000, become modulated by the serialized data stream.

As the above occurs, the resonating RF emissions signal created by RF antenna coil 2002 of the RF antenna 2000, now being impressed with a return RF emissions signal containing modulated serial data from the RF tag 3000, can be observed to have both a reduced amplitude and to contain a representation of the modulated serialized data. The RF interrogator 1000 containing certain circuitry that can detect, filter, and amplify the serialized data, then transforms a resultant signal thereof into a viable and useable data stream signal, in effect reconstructing the original data stream as provided by the RF tag 3000.

The viable and useable data stream signal is then applied to, and read by, a microcontroller device within the RF interrogator 1000, and minimally predicated on application and predetermined firmware, the RF interrogator 1000, then performs certain desired real-world functions, one of which is that of indicating whether or not a critical alignment condition of the RF tag to the RF antenna exists, and by various means, which include, but are not limited to visual or audio means, or a computer apparatus 6000 or a printer apparatus 7000.

The following descriptions provide yet further detail with regard to FIG. 1, and as relates to each main sub-system component of the present disclosure.

Figure 2A:
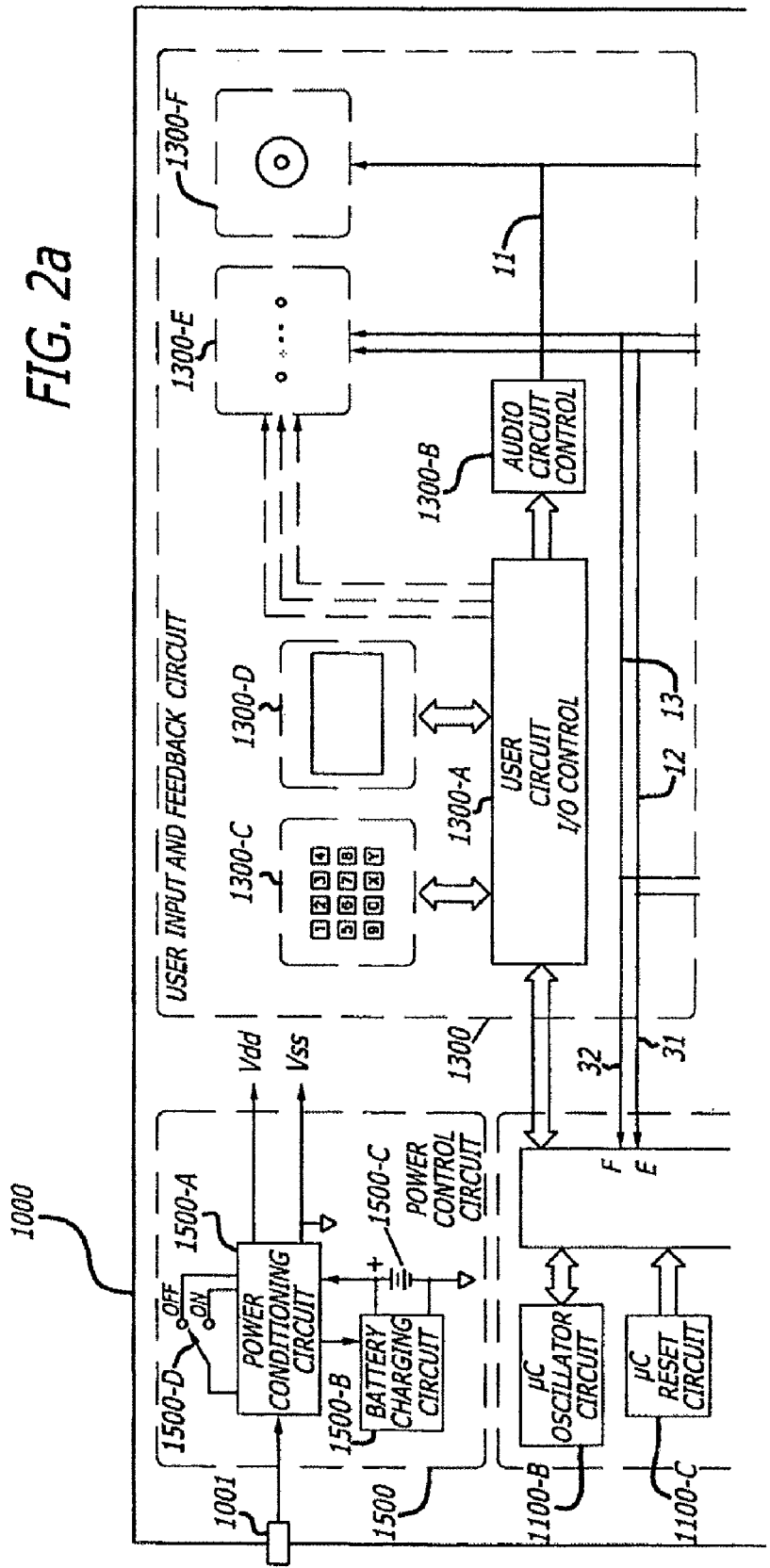
FIGS. 2a and 2b depict a subsystem block diagram of an embodiment of an RF interrogator according to the present disclosure.
Figure 2B:
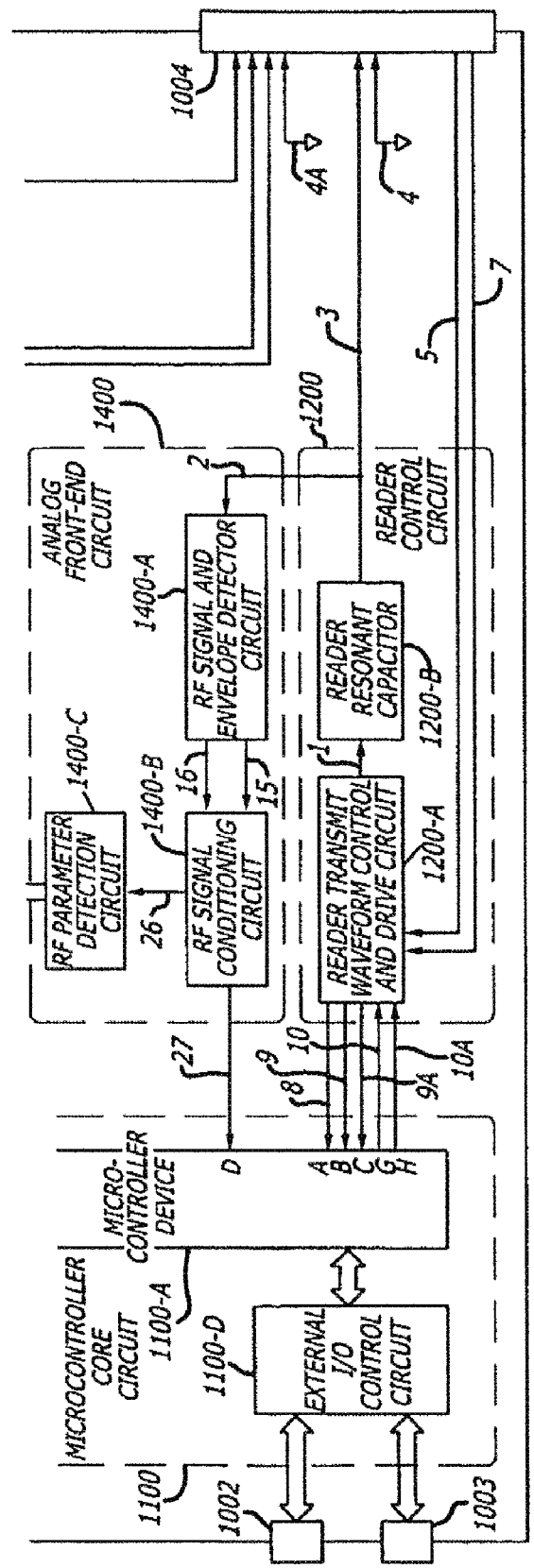

Now referencing FIG. 2, one will note multiple circuit sections within the block identified as 1000, "RF interrogator," wherein there is illustrated the five main circuit components to the RF interrogator, identified as a power control circuit 1500, microcontroller core circuit 1100, user input and feedback circuit 1300, analog front-end 1400, and antenna control circuit 1200.

Three of the five main circuit components, noted as power control circuit 1500, microcontroller core circuit 1100, and user input and feedback circuit 1300, remain entirely non-complex, and can be constructed by various means in various ways to provide the functions indicated. Intensive detail therefore, is not felt required of these the three main circuit components; thusly, abbreviated descriptions thereof will more than adequately suffice.

However, and as may not be clear to those skilled in the art, the last two of the five main circuit components, noted as analog front-end 1400 and antenna control circuit 1200, remain not only as aspects of the present disclosure, but remain somewhat complex in nature. Therefore these last two main circuit components require more explicit detail for fully understanding the present disclosure, and such detail will also follow.

To begin, and referencing both FIGS. 1 and 2, a predetermined connector apparatus 1001 accommodates a predetermined applied external power source 5000 wherein at least one predetermined power potential may generally be applied to the power control circuit 1500 and, specifically, to the power conditioning circuit 1500-A, whereby one or more predetermined voltage potentials may be created for use by the remaining circuits of the RF interrogator 1000.

The power conditioning circuit 1500-A provides for an applied power switching device 1500-D, allowing for application control of the applied power source, whether that source be internal or external, to the remainder of the power conditioning circuit 1500-A. Also a part of the power control circuit 1500, and as an option to utilizing the applied external power source 5000, a predetermined battery device 1500-C, may be used, if desired, being particularly beneficial in certain hand-held embodiments and applications of the present disclosure.

In those applications where external power source backup or occasional freedom from an external power source is desired, provisions for a battery charging circuit 1500-B are additionally made available to charge the battery device 1500-C during those occasions when appropriate to do so and when the applied external power source 5000 is made available.

In whole then, the power control circuit 1500 may provide for either or both an externally applied power source, an internally supplied power source, and ultimately the voltage potentials that operate the whole of the RF interrogator.

The microcontroller core circuit means 1100 provides for a microcontroller device 1100-A, a microcontroller (μC) oscillator circuit 1100-B, a microcontroller (μC) reset circuit 1100-C, and an external I/O control circuit 1100-D.

The microcontroller device 1100-A provides for multiple functions, not limited to, but including those functions of certain I/O ports and/or pins, internal RAM and ROM or E2 memory, etc., an internal clock generator, reset control, at least one internal timer, and perhaps, an A/D converter.

The microcontroller (μC) oscillator circuit 1100-B may be composed of a crystal oscillator device and two capacitor devices, typically providing means not only for enhanced oscillation stability over temperature, but for a broad range of frequencies at which the microcontroller device 1100-A may operate or remain (potentially) constructed of a resistor device and a capacitor device in series, providing means for reduced oscillation stability over temperature, and a minimum frequency at which the microcontroller device 1100-A may operate.

The microcontroller (μC) reset circuit 1100-C may be constructed of a resistor device and a capacitor device in series, provides means for the microcontroller device 1100-A to note when adequate operational power is dependably available, as well as allows the microcontroller device 1100-A to detect or determine when to reset various internal registers in preparation for proper operation to occur.

The external I/O control circuit 1100-D may be constructed of simple logic-gate devices or communications port function-specific I/O devices, such as serial or parallel communications devices, wherein the microcontroller device 1100-A may effect communication to or with certain external devices, such as a remote printer apparatus 7000 or a remote computer apparatus, 6000, per predetermined external connector apparatus 1003 and 1002, respectively.

The user input and feedback circuit 1300 provides for a user keyboard apparatus 1300-C, a user LCD (or other "like" display) apparatus 1300-D, an LED (light emitting diode) display 1300-E, an audio control circuit 1300-B, an audio device 1300-F, and a user input/output (I/O) control circuit 1300-A.

The user I/O control circuit 1300-A, in effect a signal multiplexer, is constructed so as to allow means wherein certain discrete logic signals or data bus signals, etc., can be steered to or from, and between the microcontroller device 1100-A and the user keyboard apparatus 1300-C, the user LCD (or other "like" display) apparatus 1300-D, the LED (light emitting diode) display 1300-E, and the audio control circuit 1300-B.

Further, the user I/O control circuit 1300-A may be generally constructed of simple logic gate devices or one or more (perhaps tri-state) 8-bit latch or bus circuit devices, so as to provide means for the microcontroller device 1100-A to interface with the user keyboard apparatus 1300-C, user LCD (or other "like" display) apparatus 1300-D, LED (light emitting diode) display 1300-E, and the audio control circuit 1300-B, when need be, and with the benefit of requiring only a minimized quantity of I/O or port pins on the microcontroller device 1100-A.

The user keyboard apparatus 1300-C enabled by the user I/O control circuit 1300-A, and generally constructed of two or more push button switches, provides means for a given user to input certain predetermined data, instructions, and commands, etc., to the microcontroller device 1100-A.

The user LCD (or other "like" display) apparatus 1300-D, enabled by the user I/O control circuit 1300-A, provides means for a given user to note inputted user data or instructions or commands, etc., to the microcontroller device 1100-A as well as obtain feedback related to user-inputted information and certain other data or predetermined operational parameters as may be provided by the RF interrogator 1000 and the RF transducer alignment system 8000.

Further, the user LCD (or other "like" display) apparatus 1300-D may also provide additional means required for a backlighting function, particularly beneficial for RF transducer alignment system operation in dimly lit areas.

The LED (light emitting diode) display 1300-E enabled by the user I/O control circuit 1300-A, and composed of one or more LED devices and a current limiting series resistor device for each installed LED device, provides quick feedback for a given user, whereby one can note certain predetermined operational parameters of the RF interrogator 1000 and the RF transducer alignment system 8000, such as when a "ready to operate" state has been established or when a given RF tag is detected, and other parametric nuances as required by application or as desired.

Figure 3:
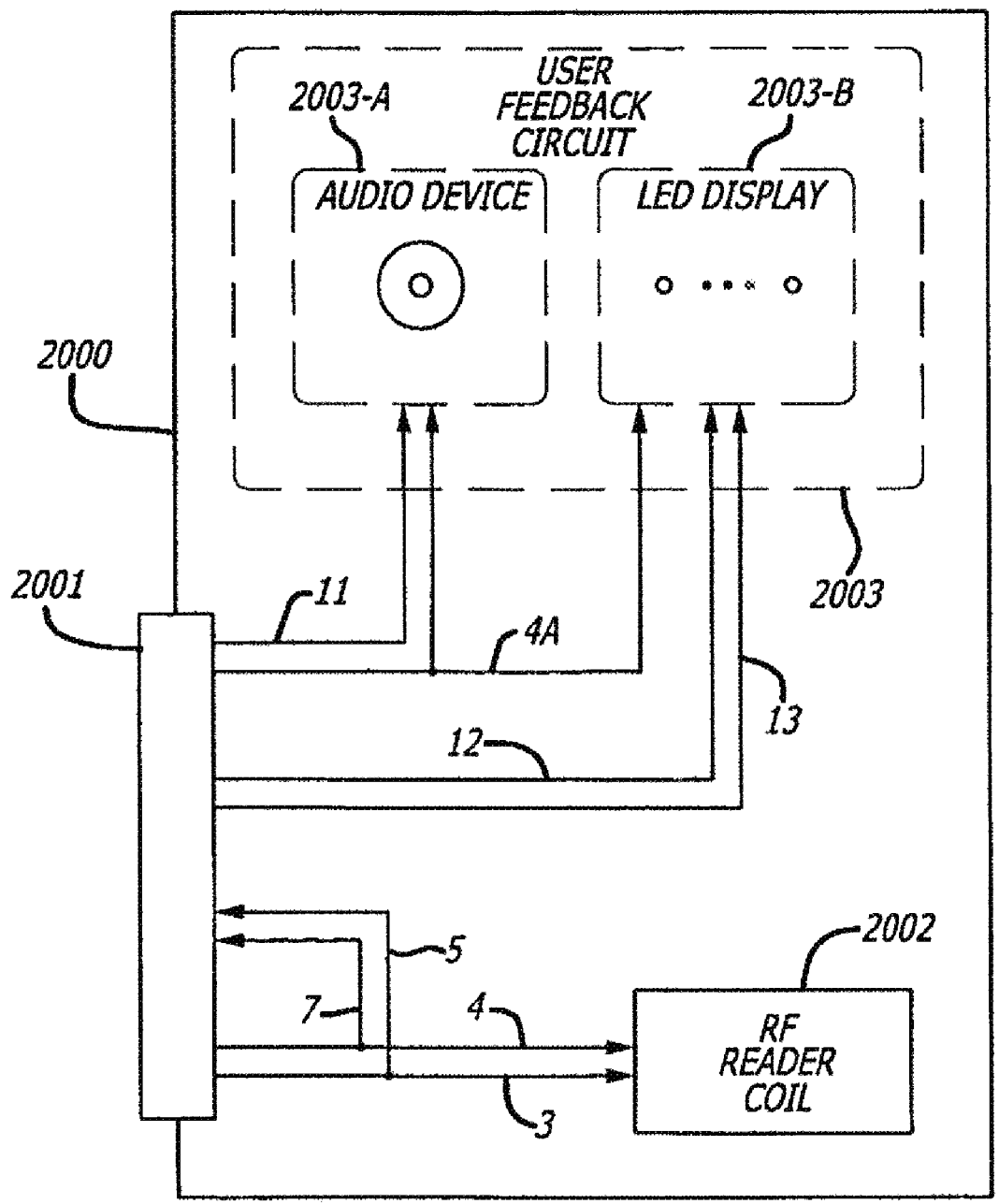
FIG. 3 depicts a subsystem block diagram of an embodiment of an RF antenna according to the present disclosure.

Further, one or more certain signals of the LED (light emitting diode) display 1300-E may additionally be passed on to a connector device 1004 so that the signals may then be passed through the antenna umbilical cable 4000 to the RF antenna means 2000, and (now referencing FIG. 3) through a connector apparatus 2001 to the user feedback circuit 2003 and ultimately to the LED display 2003-B (also of FIG. 3).

Referring again to FIG. 2, the audio control circuit 1300-B, enabled by the user I/O control circuit 1300-A, may be composed of a simple FET transistor, or like device, or a gated tone or voice generator circuit, of which, and in either case, a signal thereof is ultimately passed to the audio device 1300-F so as to create an audible source of feedback for a given user and as may additionally concern specific system parameter detection.

The audio device 1300-F may be comprised of a standard speaker element or a piezo device.

Further, a signal of the audio control circuit 1300-B may additionally be passed on to a connector device 1004 so that the signal may then be passed through the antenna umbilical cable 4000 to the RF antenna 2000 and (now referencing FIG. 3 again) through a connector apparatus 2001 to the user feedback circuit 2003 and ultimately to the audio device 2003-A (also of FIG. 3).

Referencing FIG. 2 once again, the three non-complex circuit components of the RF interrogator 1000, include the power control circuit 1500, which both receives and applies the voltage potential necessary for proper operation of the RF interrogator 1000; the microcontroller core circuit 1100-A, which provides the intelligence and means to allow desired functionality of the RF interrogator means 1000; and the user input and feedback circuit 1300, which provides for allowing intimate user control of, and feedback from, the RF interrogator 1000.

Referring now to FIGS. 1 and 3, the RF antenna 2000 is described. The RF antenna 2000, is composed of a connector apparatus 2001, which allows for applying certain circuit signals from the RF interrogator means 1000 to the RF antenna means 2000, as well as for applying certain circuit signals from the RF antenna 2000 to the RF interrogator 1000; an RF antenna coil 2002; and a user feedback circuit 2003.

An input signal 11, a third applied signal, carries one or more waveforms or frequencies, which become audibly notable as sound when presented to a first pin of item 2003-A, an audio device, of user feedback circuit 2003. The audio device 2003-A may be comprised of a standard speaker element or a piezo device.

Input signal 12, a fourth applied signal, is presented to a first pin of a first LED device of item 2003-B of user feedback circuit 2003 to indicate RF tag detection has occurred.

Input signal 13, a fifth applied signal, is presented to a first pin of a second LED device of item 2003-B of user feedback circuit 2003 to indicate that a valid data stream signal has been detected.

Input signal 4A, a sixth applied signal, is presented to the remaining and second pins of the audio device 2003-A, the first LED device of item 2003-B, and finally, the second LED device of item 2003-B, all of user feedback circuit 2003, providing for a second circuit ground signal.

Input signal 3, a first applied signal, composed of a predetermined frequency when active, is presented to a first lead of an RF antenna coil apparatus 2002 of the RF antenna 2000, as means to allow for eventual resonant oscillation of the RF antenna coil apparatus 2002. As the RF antenna coil apparatus 2002 then responds to applied the input signal 3, a first EM field of flux and carrier transmit EM field of flux signal is created by the RF antenna coil apparatus 2002.

Output signal 5, a first return signal, is presented to the connector apparatus 2001 as means to allow for monitoring the eventual resonant oscillations of the RF antenna coil apparatus 2002 by the RF interrogator 1000.

Input signal 4, a second applied signal, is presented to a second lead of an RF antenna coil apparatus 2002 of the RF antenna 2000, providing for a first circuit ground signal.

Output signal 7, a second return signal, is presented to the connector apparatus 2001 as means to enable monitoring the presence of the RF antenna coil apparatus 2002 within the RF transducer alignment system 8000 by the RF interrogator 1000.

Figure 4:
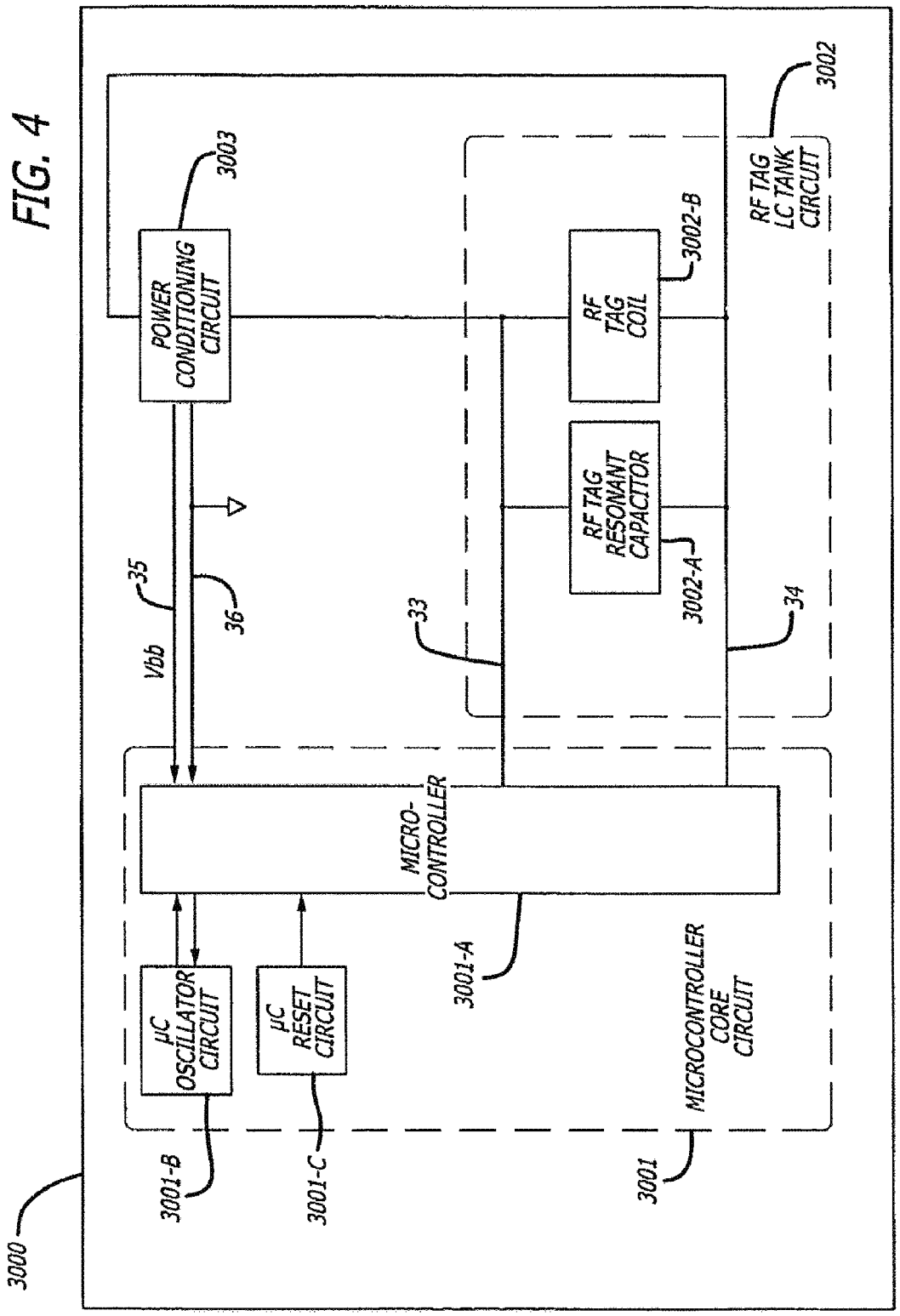
FIG. 4 depicts a subsystem block diagram of an embodiment of an RF tag according to the present disclosure.

Referring now to FIGS. 1 and 4, the RF tag 3000 is described. The RF tag 3000 is composed of a microcontroller (μC) core circuit 3001 formed of a μC oscillator 3001-B, a μC reset circuit 3001-C, and a microcontroller device 3001-A; an RF tag LC tank circuit 3002 formed of an RF tag resonant capacitor device 3002-A, and an RF tag coil apparatus 3002-B; and finally, a power conditioning circuit 3003.

The RF tag 3000, is a stand-alone apparatus that requires no on-board or attached power source for operation. As also indicated, power for the RF tag 3000, is obtained when the RF tag 3000 is brought within close proximity to a first radiated EM field of flux, as would typically be provided by the RF antenna 2000, such that the RF tag LC tank circuit 3002 becomes impressed with the first radiated EM field of flux, which then excites the RF tag LC tank circuit 3002 into self-oscillation, which as a result, produces a localized second EM field of flux.

The second EM field of flux, produced by the RF tag LC tank circuit 3002, is then radiated from the RF tag LC tank circuit 3002 and the RF tag 3000.

A portion of the energy created by the second EM field of flux produced by the RF tag LC tank circuit 3002 is then applied to the power conditioning circuit 3003 composed of a rectifier circuit and a capacitor device, whereby a second internal signal and circuit ground signal 36 are created. A predetermined voltage potential of a D.C. nature is created, all of which is then applied, via a first internal signal 35 to the microcontroller device 3001-A, providing for operational power.

When the microcontroller device 3001-A asserts the predetermined voltage potential to be stable, the microcontroller device 3001-A begins to dampen the oscillations produced by the RF tank LC circuit 3002 by means of applying a predefined and "stored" data stream signal to the base of an internal FET transistor device, thereby enabling the FET, whose drain and source pins are, effectively, placed across third and fourth internal signals, 33 and 34, respectively. By virtue of physical attachment and the enabled FET, the impresses the second EM field of flux produced by the RF tag LC tank circuit 3002 with the "stored" data stream signal, culminating in a modulated second EM field of flux and a data transmit or return EM field of flux signal.

Because the construction and operation of items 3001-B and 3001-C have been generally described earlier, and as related to the RF interrogator items 1100-B and 1100-C, respectively, repeat discussion is unnecessary. Suffice it to say, item 3001-B provides means by which the microcontroller device 3001-A might obtain a system clock signal for operation, and that item 3001-C provides means by which the microcontroller device 3001-A might obtain a reset signal so as to begin operation.

Turning next to the antenna control circuit 1200 and analog front-end circuit 1400, the remaining two, and more complex, circuit components of the RF interrogator 1000.

Figure 5:
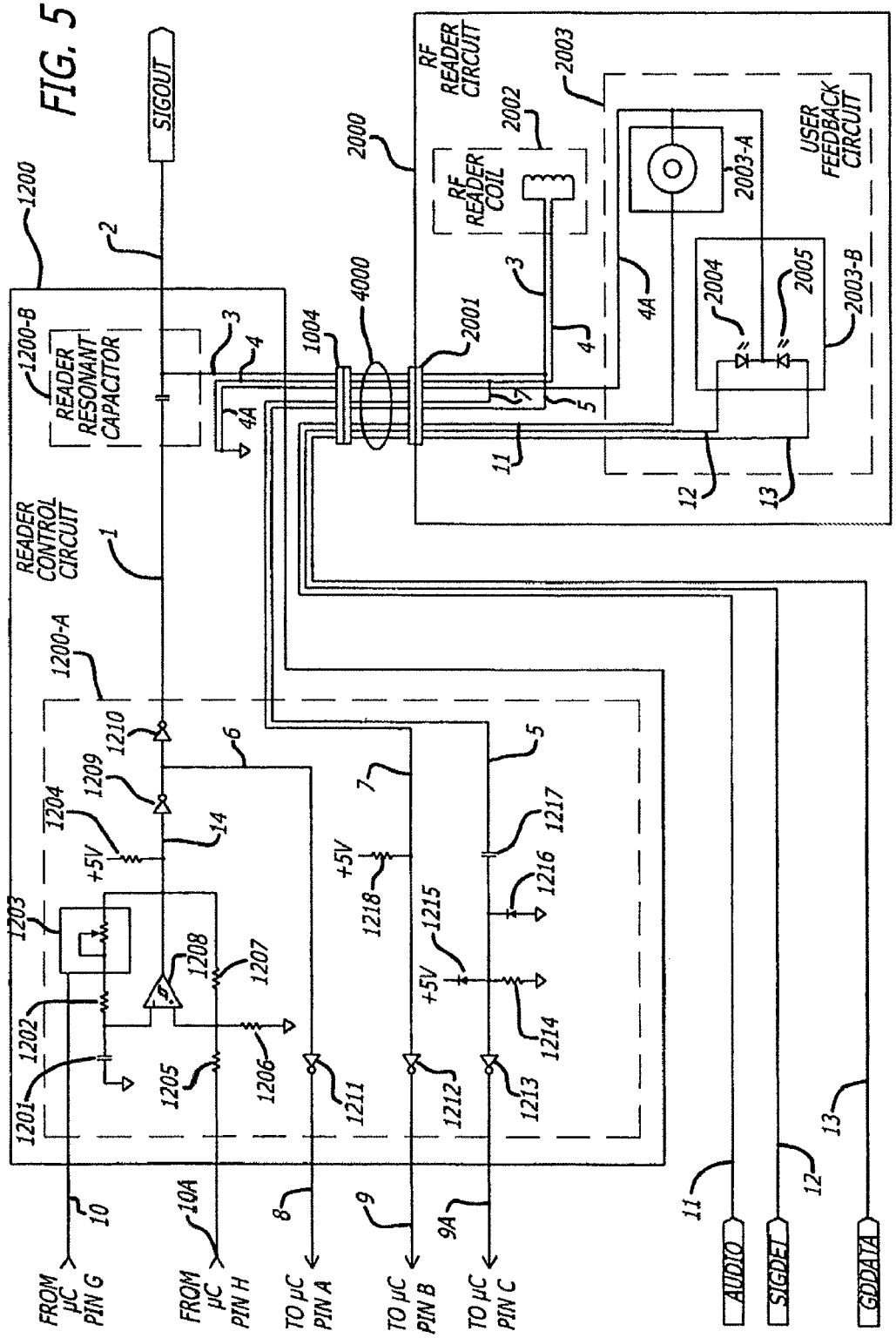
FIG. 5 depicts a portion of a schematic diagram of an embodiment of the RFID transducer alignment system according to the present disclosure.

Referring to FIG. 2 for an overview, and referencing FIG. 5 for clarity of this section, one will note item 1200, the antenna control circuit is composed of antenna transmit waveform control and drive circuit 1200-A, and antenna resonant capacitor 1200-B.

The antenna transmit waveform control and drive circuit 1200-A provides means whereby a predetermined square wave signal, in this embodiment, is generated by item and circuit component 1208, a comparator device, and items and circuit components 1201 through 1207, which together provide for the antenna transmit waveform control portion of the antenna transmit waveform control and drive circuit 1200-A.

The comparator device 1208 is gated, and thus enabled or disabled, by means wherein resistor 1205 is made responsive to a selected output pin and signal 10A from the microcontroller device 1100-A, wherein a first and left lead and input to resistor 1205 is alternatively pulled logically HI or LO.

Resistors 1205 and 1206 create a center voltage potential of ½ of the applied circuit voltage, in this embodiment of 2.5 volts D.C., when the first and left lead and input to resistor and item 1205, is pulled logically HI. The center voltage potential, for example 2.5 volts, becomes the baseline for oscillation to occur about the comparator device 1208. When the first and left lead and input to resistor 1205 is pulled logically LO, the comparator device 1208 is disabled from oscillating.

If gating the comparator device 1208 is not required for a particular application or embodiment, the first and left lead and input to resistor 1205 may be tied directly to +5V instead.

Resistors 1202 and 1203 and capacitor and item 1201 provide means for actual oscillation about the comparator device 1208 to occur.

As illustrated, resistor 1203 is programmably made to be variable, wherein the actual resistance value of resistor 1203 is intimately controlled by pin G, noted as signal 10, from the microcontroller device 1100-A, and thus ultimately provides for variation in the oscillation frequency about the comparator device 1208, which, based on the components illustrated, allows for an oscillation and frequency range of approximately 113 kilohertz to 165 kilohertz. For this embodiment it should be noted the selected frequency of oscillation was set to 119.5 kilohertz.

As well of note, resistor 1203 can alternatively be replaced with a manual variable-resistor device.

Because the circuit component 1208, the comparator device, allows only for an open-collector transistor output, which provides for a logical LO state and output signal when turned on, resistor 1204, a pull-up device, must be installed to accommodate a logical HI state and output signal when the open-collector transistor is turned off, which collectively then provides for the required two-state duty cycle.

Thus, the collective junction of the open-collector transistor output of the circuit component 1208, the comparator device, and the resistors 1204, 1203, and 1207, provide not only for the required two-state duty cycle, but an oscillating circuit signal 14 of 119.5 kilohertz, having the form of a square wave.

For an alternative embodiment, circuit components 1201 through 1208 can be wholly replaced by a crystal clock oscillator circuit and a divide-by circuit, as an example, which together, can also provide for a square wave output. However, frequency changes, if desired, are limited and made more difficult, in that by the very nature of such the circuitry only fundamental harmonics of the crystal oscillator can be easily realized, to with: f, f/2, f/4, etc.

As an example, the output of a 4 megahertz crystal oscillator circuit applied to a divide-by 32 logic device will easily provide for a 125 kilohertz square wave output, but it will not easily accommodate providing for a 119.5 kilohertz square wave output. Neither will the logic device, set to divide by 16, or divide by 64, accommodate providing for a 119.5 kilohertz square wave output.

The square wave signal 14 is then applied to the input of circuit component 1209, an inverter device, which inverts the square wave signal. This resultant signal 6 is then applied to the inputs of two following inverter devices 1210 and 1211 so as to buffer the resultant signal 6 and perform a signal phase correction.

The output of circuit component and item 1211, noted as signal 8, is then fed back to an input pin A of the microcontroller device 1100-A so as to provide means whereby the oscillation frequency of the circuit component and item 1208 can be monitored.

The circuit component 1210 through its output, noted by signal 1, provides for the antenna transmit waveform drive portion of the antenna transmit waveform control and drive circuit 1200-A, whereby the output signal 1 is fed forward and applied to a first pin of a predetermined antenna resonant capacitor 1200-B.

The remaining and second pin of the antenna resonant capacitor 1200-B is ultimately made to connect to a first lead of an RF antenna coil 2002 by means of circuit signal 3 and connector apparatus 2001, whereupon oscillations of the predetermined frequency can be observed when the remaining and second lead of the RF antenna coil 2002 is connected to circuit ground through circuit signal 4 and the connector apparatus 2001.

Figure 6:
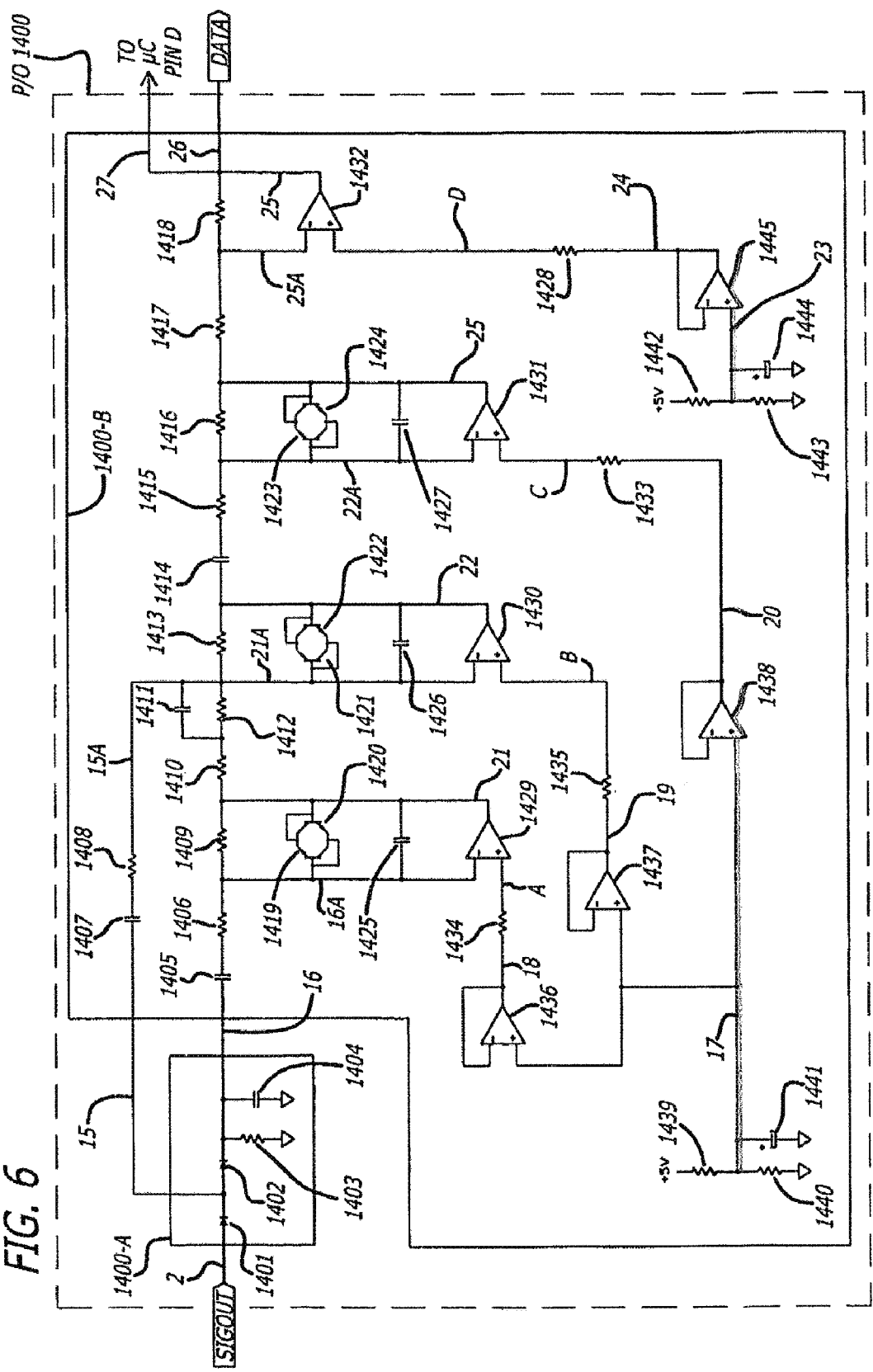
FIG. 6 depicts a portion of a schematic diagram of an embodiment of the RFID transducer alignment system according to the present disclosure.

The output signal 2, identified by the nomenclature "SIGOUT," also attached to the remaining and second pin of the antenna resonant capacitor 1200-B, provides means by which the oscillations of a predetermined frequency upon circuit signal 3 can be passed on to that circuitry identified as analog front-end 1400 of FIG. 2, and in particular, to the anode of the diode 1401 of FIG. 6, of a signal detection circuit 1400-A, which will collectively be discussed shortly.

As expected, the output signal 2, which is exactly the same as the circuit signal 3, is fundamentally a sine wave and remains of an alternating voltage potential, which greatly exceeds that of the antenna transmit waveform drive signal 1. Component values and resonance factors of both the antenna resonant capacitor 1200-B and the RF antenna coil 2002, working in synchronicity with each other, and, depending on the frequency of oscillations supplied by signal 14, together provide means for the amplitude exacerbation observed in the output signal 2.

In fact, peak-to-peak voltages of greater than 150 volts can be observed in output signal 2 when maximum resonance is sought. However, and for best operation disclosure, the frequency of oscillations supplied by signal 14 are generally made to be detuned by about 7% from the inherently derived resonant frequency, as calculated by standard LC resonance equation [i.e., ½Π√LC] and the actual values of the antenna resonant capacitor 1200-B and the RF antenna coil 2002, which, and also as expected, somewhat reduces the amplitude of the circuit signal 3 and the output signal 2, yet does not affect or negatively impact operation of the interrogator 1000 in any way.

There is a portion of FIG. 5 that contains a schematic of the RF antenna circuit 2000, which therein provides for a multiplicity of input/applied and output/return signals at the connector apparatus 2001, as addressed earlier in this section.

Internal circuit signal 7 of the RF antenna circuit 2000 provides means whereby the RF interrogator 1000 might monitor the presence of circuit signal 4 and the RF antenna circuit 2000, and particularly, the presence of the RF antenna coil apparatus 2002, so as to typically either note and indicate the lack of a main sub-system component, and so at a minimum disable the comparator device 1208, or proceed into normal operations and enable the comparator device 1208.

If the antenna umbilical cable apparatus 4000 is attached to item 1004, a predetermined connector apparatus and component of the antenna control circuit 1200 and, if the RF antenna circuit 2000 is attached to the antenna umbilical cable apparatus 4000, then the internal circuit signal 7 of the RF antenna circuit 2000 will be presented to the antenna control circuit 1200 and to the resistor component 1218, as well as to the input of the inverter device 1212. The output of the inverter device 1212 will then be forced logically HI, indicating to the microcontroller devices 1100-A by means of signal 9 being presented to the μC input pin B that the RF antenna circuit 2000 is indeed present.

However, if the antenna umbilical cable apparatus 4000 is not attached to the connector apparatus 1004 or if the RF antenna circuit 2000 is not attached to the antenna umbilical cable apparatus 4000, then the internal circuit signal 7 of the RF antenna circuit 2000 will not be presented to the antenna control circuit 1200 and to the resistor component 1218, as well as to the input of the inverter device 1212. In this case, the output of the inverter device 1212 will then be forced logically LO, indicating to the microcontroller devices 1100-A by means of signal 9 being presented to the μC input pin B that the RF antenna circuit 2000 is absent.

As well, internal circuit signal 5 of the RF antenna circuit 2000 provides means whereby the RF interrogator 1000 might monitor the presence of the circuit signal 3 and the eventual resonant oscillations of the RF antenna coil apparatus 2002 of the RF antenna circuit 2000 so as to typically note and indicate the lack of the eventual resonant oscillations or note and indicate the frequency of the eventual resonant oscillations or both.

If the antenna umbilical cable apparatus 4000 is attached to the connector apparatus 1004, and if the RF antenna circuit 2000 is attached to the antenna umbilical cable apparatus 4000, then the internal circuit signal 5 of the RF antenna circuit 2000 will be presented to the antenna control circuit 1200 by means of a first lead of the capacitor device 1217, which acts to A.C. couple the internal circuit signal 5 of the RF antenna circuit 2000 to the antenna control circuit 1200.

The second and remaining lead of the capacitor device 1217 passes a portion of the internal circuit signal 5 applied to the first lead of circuit component and capacitor device 1217 as a resultant signal on to the diode device 1216 and the cathode thereof, and the diode device 1215 and the anode thereof, and to the resistor device 1214.

When the eventual resonant oscillations from the RF antenna coil apparatus 2002 are present, the diode devices 1215 and 1216 act to clip any excess and undesired voltage peaks from the resultant signal provided for by means of the second lead of the capacitor device 1217.

In this instance, the resistor device 1214 acts to reference the resultant signal provided for by means of the second lead of the capacitor device 1217 to circuit ground.

The resultant signal, provided for by means of the second lead of the capacitor device 1217, is then applied to the input of the inverter device 1213, whereby the output of the inverter device 1213 will invert the resultant signal and pass the inverted resultant signal on to the microcontroller devices 1100-A by means of signal 9A being presented to the μC input pin C.

However, if the antenna umbilical cable apparatus 4000 is not attached to the connector apparatus 1004, or if the RF antenna circuit 2000 is not attached to the antenna umbilical cable apparatus 4000, then the internal circuit signal 5, now an open circuit, will still be presented to the antenna control circuit 1200 by means of a first lead of the capacitor device 1217, but since no signal of oscillation will be present, the capacitor device 1217 becomes, in effect, an open circuit as well.

Therefore, and without the resistor device 1214 being in place, the second lead of the capacitor device 1217 and its voltage potential would be considered "floating." Thusly, in this instance, the resistor device 1214 acts to reference the input of the inverter device 1213 to circuit ground.

In addition, the diode devices 1215 and 1216 also, in essence, become open circuits.

The effect of having no resultant signal, as would otherwise normally be provided for by means of the second lead of the capacitor device 1217, is that the input of the inverter device 1213, now referenced to circuit ground the resistor device 1214, provides a steady state logical HI signal as an output to the microcontroller devices 1100-A by means of signal 9A being presented the to μC input pin C.

Certain undiscussed circuit signals of FIG. 5 and the RF antenna circuit 2000 identified as circuit signal 11 and by the nomenclature "AUDIO," as circuit signal 12 and by the nomenclature "SIGDET," and as circuit signal 13 and by the nomenclature "GDDATA," shall now be elaborated upon.

The origin of these three circuit signals is to be found in FIG. 6, which has yet to be discussed; however, these signals have been somewhat addressed earlier when the RF antenna circuit 2000 was described.

The input circuit signal 11, identified by the nomenclature "AUDIO," is caused to be presented to the RF antenna circuit 2000, in part by means of the connector apparatus 2001 and, ultimately, to a first pin of the audio device 2003-A. The input circuit signal 11 will be either at circuit ground potential, providing for "off" functionality of the circuit component and predetermined audio device 2003-A, or applied to one or more waveforms or frequencies, which become audibly notable as sound, when presented to the first pin of the audio device 2003-A, thus providing control for activation of the audio device 2003-A, providing in addition for "on" functionality.

The input circuit signal 12, identified by the nomenclature "SIGDET," is caused to be presented to the RF antenna circuit 2000 by means of the connector apparatus 2001 and, ultimately, to a first pin of the first LED device 2004. The input circuit signal 12 will be either held at +5V if SIGDET is active, or applied to the circuit ground potential if SIGDET is not active to the first pin of the LED 2004 or user feedback circuit 2003, thus providing means to toggle the LED 2004 on and off, respectively.

The input circuit signal 13, identified by the nomenclature "GDDATA," is caused to be presented to the RF antenna circuit 2000, by means of the connector apparatus 2001 and, ultimately, to a first pin of the second LED device 2005. The input circuit signal 13 will be either held at +5V if GDDATA is active, or applied to the circuit ground potential if GDDATA is not active, to the first pin of the LED 2005 of user feedback circuit 2003, thus providing means to toggle the LED 2005 on and off, respectively.

The remaining undiscussed circuit signals of FIG. 5 and the RF antenna circuit 2000 shall now be addressed.

Circuit signal 4A is presented to the remaining and second predefined pins of the audio device 2003-A, the first LED device 2004, and the second LED device 2005 of item 2003-B, all of user feedback circuit 2003, providing for a second circuit ground signal of and to the RF antenna circuit means 2000 by means of the connector apparatus 2001.

Circuit signal 3, applied by means of the connector apparatus 2001, and having one or more predetermined frequencies, at a minimum, when active, is presented to a first lead of an RF antenna coil apparatus 2002 as a means to allow for eventual resonant oscillation of the RF antenna coil apparatus 2002. As the RF antenna coil apparatus 2002 responds to an actively applied input signal 3, a first EM field of flux and carrier transmit EM field of flux signal is created by the RF antenna coil apparatus 2002.

Turning next to FIG. 6, which illustrates a first partial drawing of the analog front-end 1400, and which is comprised of RF signal and envelope detector circuit 1400-A and RF signal conditioning circuit 1400-B.

The output signal 2, first illustrated in FIG. 5, and identified by the nomenclature "SIGOUT," is applied to the anode of the diode 1401, the first circuit component and signal rectifier of the RF signal and envelope detector circuit 1400-A.

The cathode of the diode and item 1401, noted as raw circuit signal 15, is then applied to the anode of the diode 1402, a second circuit component and signal rectifier of the RF signal and envelope detector circuit 1400-A, as well as is applied to the capacitor 1407.

The cathode of the diode 1402 is then applied to a resistor device 1403 and a capacitor device 1404, whereby a resultant detected signal 16 is both created and referenced to the circuit ground. The resultant detected signal 16 remains considerably reduced in amplitude from the applied output signal 2, and is comprised, in part, of a partially modulated carrier transmit signal.

As the RF antenna 2000 is brought within close proximity of the RF tag 3000 (or vise versa), the RF antenna coil apparatus 2002 becomes impressed with the data-modulated return EM field of the flux signal provided by the RF tag 3000. As this occurs, the data-modulated return EM field of flux signal provided by the RF tag 3000 appears in part at the circuit signals 3 and 2 and first lead of the RF antenna coil apparatus 2002 as a backscatter signal.

The resultant detected signal 16 displays a multiplicity of frequency components, comprised at a minimum of the carrier transmit signal of 100 kilohertz or greater, as provided by the RF antenna coil apparatus 2002, the data receive signal comprised of 100 kilohertz or greater, and modulated and provided by the RF tag 3000, as the backscatter, stray EMI/EMF signals, and generally unavoidable internal circuit noise.

Since the resultant detected signal, 16, is of an abbreviated amplitude, and since it is composed of a myriad of frequency components, additional circuitry is required so as to extract the desired data signal component, as first provided by the RF tag 3000 from the remaining frequencies and undesired signal components.

Turning next to the RF signal conditioning circuit 1400-B of the analog front-end circuit 1400, the resultant detected signal 16 is applied to the capacitor device 1405 and resistor device 1406, which together act, in part, as a first filter means, and which provide a first variant signal of the resultant detected signal 16 to the non-inverting input of the amplifier device 1429. The resultant detected signal 16 is applied to a first lead of the capacitor device 1405, whose remaining and second lead is applied to a first lead of the resistor device 1406, which the components 1405 and 1406 together act, in part, as a first filter means, and which provide a first variant signal, noted as 16A, derived from the resultant detected signal 16 to the inverting input of the operational amplifier device 1429 and to a first lead of the resistor device 1409, whose remaining and second lead is applied to the output of the operational amplifier 1429.

The operational amplifier 1429 amplifies the first variant signal 16A according to the value relationship of two resistors 1406 and 1409 and provides an amplified version of the first variant signal 16A at its output as a first amplified signal, noted as signal 21.

Applied around the non-inverting input and the output of the operational amplifier 1429, are two NPN transistors, configured as virtual diode limiter devices 1419, 1420.

The use of the NPN transistors 1419 and 1420 is because the parameter of "distance sensing" is a substantial prerequisite and factor in the design of the present disclosure, and as such common diode devices, such as 1n4148's, could not be incorporated because they exhibit instability, high leakage and conductance, and unsuitable capacitance, even at room temperature, especially observable when applied signals to the common diode devices are approximately +/−70 or so millivolts in amplitude or less.

The present disclosure allows for sensing applied signals less than 70 millivolts in amplitude, therefore common diode devices non-ideally affect desired signal integrity when amplified. To clarify, the fundamental reason for using NPN transistors 1419 and 1420 is to provide for a more stable signal at the first amplified signal 21 when applied first variant signal is only of a few millivolts in nature. Resultant detected signal 16 contains only a few millivolts of observable backscatter and data stream signal component.

The capacitor device 1425 acts to provide enhanced signal integrity and stability and provides frequency compensation about the operational amplifier 1430.

Resistor device 1439, resistor device 1440, and capacitor device 1441 are utilized to obtain a predetermined voltage of 2.5 volts, by means wherein the resistor devices 1439 and 1440, by virtue of their physical incorporation and intrinsic values, divide the applied circuit voltage by 2, and whereafter the circuit component and capacitor device 1441 acts as a filter and signal stabilizer for the voltage of 2.5 volts, noted as signal 17.

To overcome certain impedance factors associated with the resistor devices 1439, 1440, and the capacitor device 1441, the signal 17 is applied to the non-inverting inputs of 3 predetermined operational amplifiers, noted as items 1438, 1437, and 1436, wherein each of which is configured as voltage followers.

The operational amplifiers 1438, 1437, and 1436, each have at their respective outputs, i.e., signals 20, 19, 18, a voltage signal that is also 2.5 volts, but which the signals are each now of a lo-impedance nature. The signals 20, 19, 18, are then applied to certain other operational amplifiers (items 1431, 1430, and the item 1429, respectively) as first circuit voltage reference signals C, B, and A, respectively.

Thus, signal 18 is applied to a first lead of the resistor 1434, the value of which was so chosen to approximately equal the parallel resistance value of the resistors 1406 and 1409 so as to reduce offset errors at the operational amplifier 1429. The remaining and second lead of the resistor 1434, as signal A, a first circuit voltage reference signal, is then applied to the non-inverting input of the operational amplifier 1429, completing the desired circuit about the operational amplifier 1429.

The first amplified signal, 21, outputted from the operational amplifier 1429, is then applied to a first lead of the resistor 1410, whose remaining and second lead is applied to a first lead of the resistor 1412, whose remaining and second lead is then applied to the inverting input of the operational amplifier 1430 and a first lead of the resistor 1413, whose remaining and second lead is applied to the output of the operational amplifier 1430.

However, the resistor 1411 has attached across it a capacitor 1411, which, in synchronicity with the resistors 1410 and 1412, form a second filter means.

In addition, the raw input signal 15 provided by both the cathode of the diode 1401 and the anode of the diode 1402, is as shared above, applied to a first lead of the capacitor 1407, whose remaining and second lead is then applied to a first lead of the resistor 1408, which together act as a third filter means. The remaining and second lead of the resistor 1408 provides for a first alternate signal of the applied output signal 2, noted as 15A, to the inverting input of the operational amplifier 1430.

The additive combination of the independent signals, as provided by the second lead of the resistor 1408, i.e., signal 15A, and the second leads of paralleled circuit components 1412 and 1411, together, provide for a second variant signal 21A.

The operational amplifier 1430 then amplifies the second variant signal 21A according to the value relationship of the resistors 1410, 1412, and 1413, and provides an amplified version of the second variant signal 21A at its output as a second amplified signal, noted as signal 22.

Applied around the inverting input and the output of the operational amplifier 1430 are NPN transistors, configured as virtual diode limiters 1421 and 1422. Referring back to the transistors 1419 and 1420, and the discussion thereof, the reason for the use of the NPN transistors 1421 and 1422 remains essentially the same as that for using the NPN transistors 1419 and 1420, and as such, need not be recounted.

Capacitor 1426 acts to provide enhanced signal integrity and stability, and it provides frequency compensation about the operational amplifier 1430.

The voltage reference signal 19 is applied to a first lead of the resistor 1435, the value of which was so chosen to approximately equal the parallel resistance value of the resistors 1410, 1412, and 1413, so as to reduce offset errors at the operational amplifier 1430. The remaining and second lead of the resistor 1435, receiving signal B, a first voltage reference signal, is then applied to the non-inverting input of the operational amplifier 1430, completing the desired circuit about the operational amplifier 1430.

The second amplified signal 22 outputted from the operational amplifier 1430 is then applied to a first lead of the capacitor 1414, whose remaining and second lead is applied to a first lead of the resistor 1415, which the components, 1414 and 1415, together act, in part, as a fourth filter and which provide a third variant signal, noted as 22A, derived from the amplified signal 22 to the inverting input of the operational amplifier 1431, and, a first lead of the resistor 1416, whose remaining and second lead is applied to the output of the operational amplifier 1431.

The operational amplifier 1431, then amplifies the third variant signal 22A according to the value relationship of resistors 1415 and 1416, and presents an amplified version of the third variant signal 22A at its output as a third amplified signal, noted as signal 25.

Applied around the inverting input and the output of operational amplifier 1431 are NPN transistors configured as virtual diode limiters 1423 and 1424. Referring back to the transistors 1419 and 1420, and the discussion thereof, the reason for the use of the NPN transistors 1423 and 1424 again remains essentially the same as that for using the NPN transistors 1419 and 1420, and as such, need not be repeated.

The capacitor 1427 acts to provide enhanced signal integrity and stability and provides frequency compensation about the operational amplifier 1431.

The voltage reference signal 20 is applied to a first lead of the resistor 1433. The value of the resistor 1433 was so chosen to approximately equal the parallel resistance value of the resistors 1415 and 1416 so as to reduce offset errors at the operational amplifier 1431. The remaining and second lead of the resistor 1433, as to signal C, a first predetermined circuit voltage reference signal, is then applied to the non-inverting input of the operational amplifier 1431, completing the desired circuit about the operational amplifier 1431.

The third amplified signal 25 outputted from the operational amplifier 1431 is then applied to a first lead of the resistor 1417, whose remaining and second lead, providing for a fourth variant signal noted as 25A derived from the amplified signal 25, is applied to the inverting input of the operational amplifier 1432, and to a first lead of the resistor 1418, whose remaining and second lead is applied to the output of the operational amplifier 1432.

The operational amplifier 1432 then amplifies the fourth variant signal 25A according to the value relationship of the resistors 1417 and 1418, and presents an amplified version of the variant signal 25A at its output as a fourth amplified signal, noted by nomenclature "DATA" and as signal 26, and a subsequent and fifth amplified signal, noted as signal 27, a final circuit signal.

The resistor 1442, and resistor 1443 are utilized to obtain a predetermined reference voltage of 2.7 volts, by means wherein the resistors 1442 and 1443, by virtue of their physical incorporation and intrinsic values, divide the applied circuit voltage, and whereafter, the capacitor 1444 acts as a filter and signal stabilizer for the reference voltage of 2.7 volts, noted now as signal 23.

To overcome certain impedance factors associated with the items 1442, and 1443, and the capacitor 1444, the signal 23 is applied to the non-inverting input of the operational amplifier, noted as item 1445, wherein the item 1445 is configured as a voltage follower apparatus, which provides at its output signal 24, a second voltage reference signal.

The signal 24 is applied to a first lead of the resistor 1428, the value of which was so chosen to approximately equal the parallel resistance value of the resistors 1417 and 1418 so as to reduce offset errors at the operational amplifier 1432. The remaining and second lead of the resistor 1432, as signal D, as the second predetermined circuit voltage reference signal, is then applied to the non-inverting input of the operational amplifier 1432, completing the desired circuit about the operational amplifier 1432.

The subsequent and fifth amplified signal, noted as final circuit signal 27, is ultimately applied to pin D of the microcontroller device 1100-A of FIG. 2, allowing for receiving the final circuit signal 27 by the microcontroller device 1100-A.

The fourth amplified signal, noted by nomenclature: "DATA" and as signal 26, is ultimately applied to the anode of the diode 1446 of the remaining portion, and second partial drawing of the analog front-end, 1400.

Figure 7:
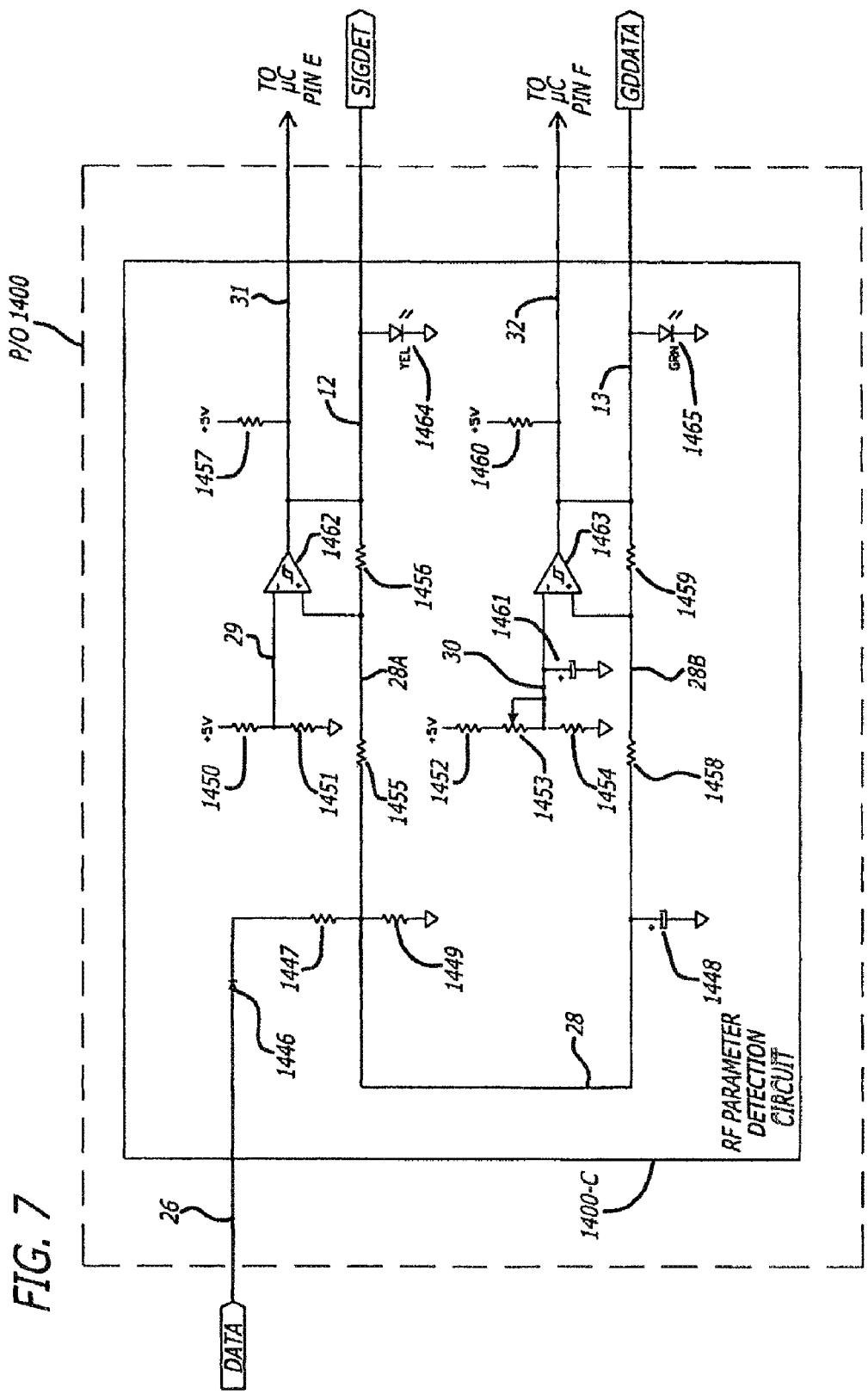
FIG. 7 depicts a portion of a schematic diagram of an embodiment of the RFID transducer alignment system according to the present disclosure.

Referring to FIG. 7 now, the fourth amplified signal, noted by nomenclature: "DATA" and as signal 26, is applied to the anode of the diode 1446, of the remaining portion of the analog front-end 1400, which comprises the RF parameter detection circuit.

The cathode of the diode 1446, a rectifier, is made to couple to a first lead of the resistor 1447, whose second and remaining lead is then coupled to a first lead of the resistor 1449 and the capacitor 1448, where together these components provide means allowing for a third predetermined circuit voltage reference signal to be generated, noted as signal 28.

The value of the resistor 1447 is chosen to establish a minimum voltage base level from which certain predetermined parameters of the final circuit signal 26 may ultimately be detected and may be construed to be predicated on the partial or whole data content of the final circuit signal 26, wherein the data content is comprised of logically HI and LO appearing waveforms. The waveforms, when integrated by additional means of the capacitor 1448, provide a predetermined D.C. voltage level to the inputs and first leads of the resistors 1455 and 1458.

The resistor 1450 has a first lead attached to the applied circuit voltage, for example, +5V, and has a second and remaining lead attached to a first lead of a resistor 1451, whereby together, the resistors 1450 and 1451 provide means for allowing the creation of a fourth predetermined circuit voltage reference signal, noted as signal 29, which is then applied to the inverting input of the comparator device 1462.

The first lead of the resistor 1455 receiving the third circuit voltage reference signal 28 has attached to its second and remaining lead a first lead of predetermined circuit component and resistor 1456, providing for a fifth predetermined circuit voltage reference signal, noted as signal 28A, and wherein the remaining and second lead of the resistor 1456 is then applied to the output of the comparator 1462.

The values of the resistors 1455 and 1456 are so chosen as to establish both a predetermined impedance and a predetermined hysteresis about the comparator 1462, wherein also, the fifth circuit voltage reference signal 28A is presented to the non-inverting input of the comparator device 1462.

As is well understood by those skilled in the art, a common voltage comparator device acts to differentiate between two independently applied input signals, i.e., the given signals presented to both the inverting AND non-inverting inputs of the common voltage comparator device, whereby the output of which will switch from a logical HI state, to a logical LO state predicated on the voltage potentials of the applied input signals.

The comparator 1462 will switch its output logically LO when the fifth circuit voltage reference signal 28A is less than the fourth circuit voltage reference signal 29, causing the LED device 1464 to remain dark, thereby indicating no given RF tag device has been detected, and providing by means of signal 12, noted by nomenclature "SIGDET," a first RF parameter detection signal, indication of the same to the RF antenna circuit, 2000, and ultimately, to the RF interrogator 1000.

Contrarily, the comparator 1462 will switch its output logically HI when the fifth circuit voltage reference signal 28A is greater than the fourth circuit voltage reference signal 29 by means of the resistor 1457 thereby causing illumination of the circuit component and LED device 1464, indicating a given RF tag device has been detected, and providing, again by means of the signal 12, "SIGDET," the first RF parameter detection signal, indication of the same to the RF antenna circuit 2000, and ultimately to the RF interrogator 1000.

The output of the comparator 1462 additionally provides for a subsequent output signal 31, ultimately presented to the input pin E of the microcontroller 1100-A, allowing for receiving the first RF parameter detection signal 31 by the microcontroller device 1100-A.

Finally, the resistor 1452 has a first lead attached to the applied circuit voltage, for example +5V, and has a second and remaining lead attached to a first lead of the resistor 1453, whose second and third remaining leads are then attached to a first lead of the resistor 1454, the junction of which, is connected to the first lead of a capacitor 1461, whereby together the items 1452-1454 and 1461 provide means for allowing the creation of a sixth circuit voltage reference signal, noted as signal 30, which is then applied to the inverting input of the comparator 1463.

The resistor 1453 is variable and provides means for obtaining a 2 to 3 volt sixth circuit voltage reference signal, noted as signal 30, and can also be of a programmable type, controlled by a microcontroller device if needed or desired.

The first lead of the resistor 1458 receiving the third circuit voltage reference signal 28 has attached to its second and remaining lead, a first lead of the resistor 1459, providing for a seventh circuit voltage reference signal, noted as signal 28B, and wherein the remaining and second lead of the resistor and item 1459 is then applied to the output of the comparator 1463.

The values of the resistors 1458 and 1459 are so chosen as to establish both a predetermined impedance and a predetermined hysteresis about the comparator 1463, wherein also the seventh circuit voltage reference signal 28B is presented to the non-inverting input of the comparator 1463.

The comparator 1463 will switch its output logically LO when the seventh circuit voltage reference signal 28B is less than the sixth circuit voltage reference signal 30, causing the LED device 1465 to remain dark, thereby indicating no valid data stream signal has been detected, and providing by means of signal 13, noted by nomenclature "GDDATA," a second RF parameter detection signal, indication of the same to the RF antenna 2000, and ultimately to the RF interrogator 1000.

Contrarily, the comparator 1463 will switch its output logically HI when the seventh circuit voltage reference signal 28B is greater than the sixth circuit voltage reference signal 30 by means of the resistor 1460, thereby causing illumination of the LED device 1465, indicating a valid data stream signal has been detected, and providing, again by means of the signal 13, "GDDATA," the second RF parameter detection signal, indication of the same to the RF antenna circuit 2000, and ultimately to the RF interrogator 1000.

The output of the comparator 1463 additionally provides for a subsequent output signal 32, ultimately presented to the input pin F of the microcontroller device 1100-A, allowing for receiving the second predetermined RF parameter detection signal 32 by the microcontroller device 1100-A.

Other RF parameter detection signals can be obtained, if desired, such as the parameter of distance, within limits, and as concerns a given RF tag device to a given RF interrogator or RF antenna device by means of additional circuitry and associative circuit signals.

Now that the new and inventive RFID interrogator alignment system, providing for broadened operational functionality and altogether new RFID applications, has been specifically described, it remains that certain aspects of the design can or may be alternatively modified from the preferred embodiment, and in lieu of the foregoing will be described in appurtenant detail. However, it is to be understood the following embodiments are given by way of example only and are not intended to suggest limits of any nature to the scope and spirit of the present disclosure, or as regards application.

As to alternative embodiments, it is assumed the reviewer now has a good understanding of the construction, function, and benefits of an embodiment of the present disclosure. In discussing the following alternate embodiments then the focus will remain on implementation or application of the alternate embodiments.

Figure 8:
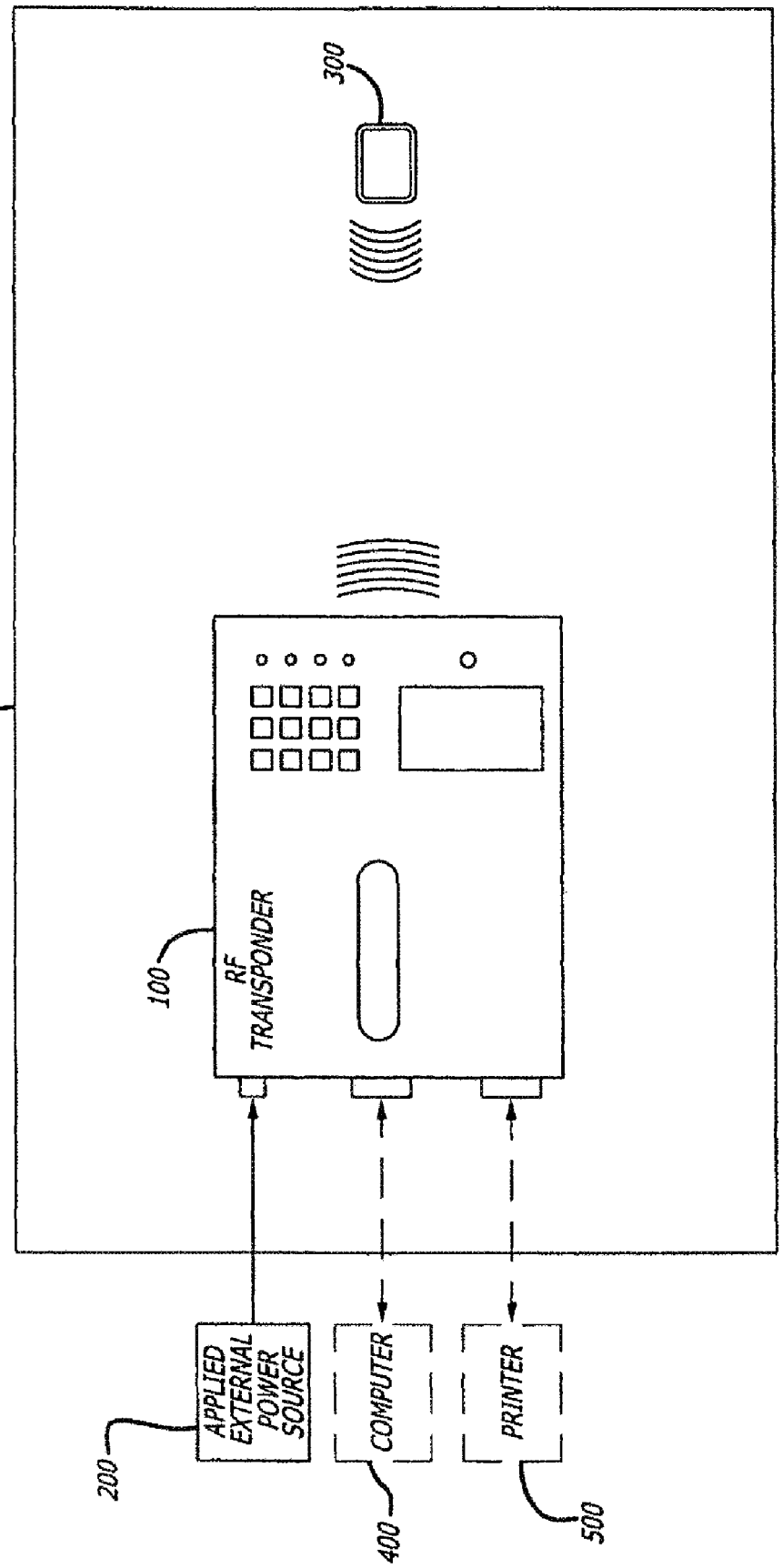
FIG. 8 is a schematic representation of an alternate embodiment of an RF transducer alignment system of the present disclosure illustrating an example of a hand-held apparatus having both an RF interrogator and an RF antenna.

FIG. 8 depicts an example embodiment and application of the present disclosure, 700, wherein a hand-held RF interrogator 100 is illustrated. The merit of items 200, 400, and 500 have already been addressed with regard to items 5000, 6000, and 7000, respectively, and need not be elaborated on here.

However, item 100 of FIG. 8 represents a top-view of a self-contained RF interrogator system package, wherein it is composed of an RF interrogator and an RF antenna. As a small enclosed, light weight package, it intrinsically offers many benefits both to end-users and as regards applications.

Figure 9:
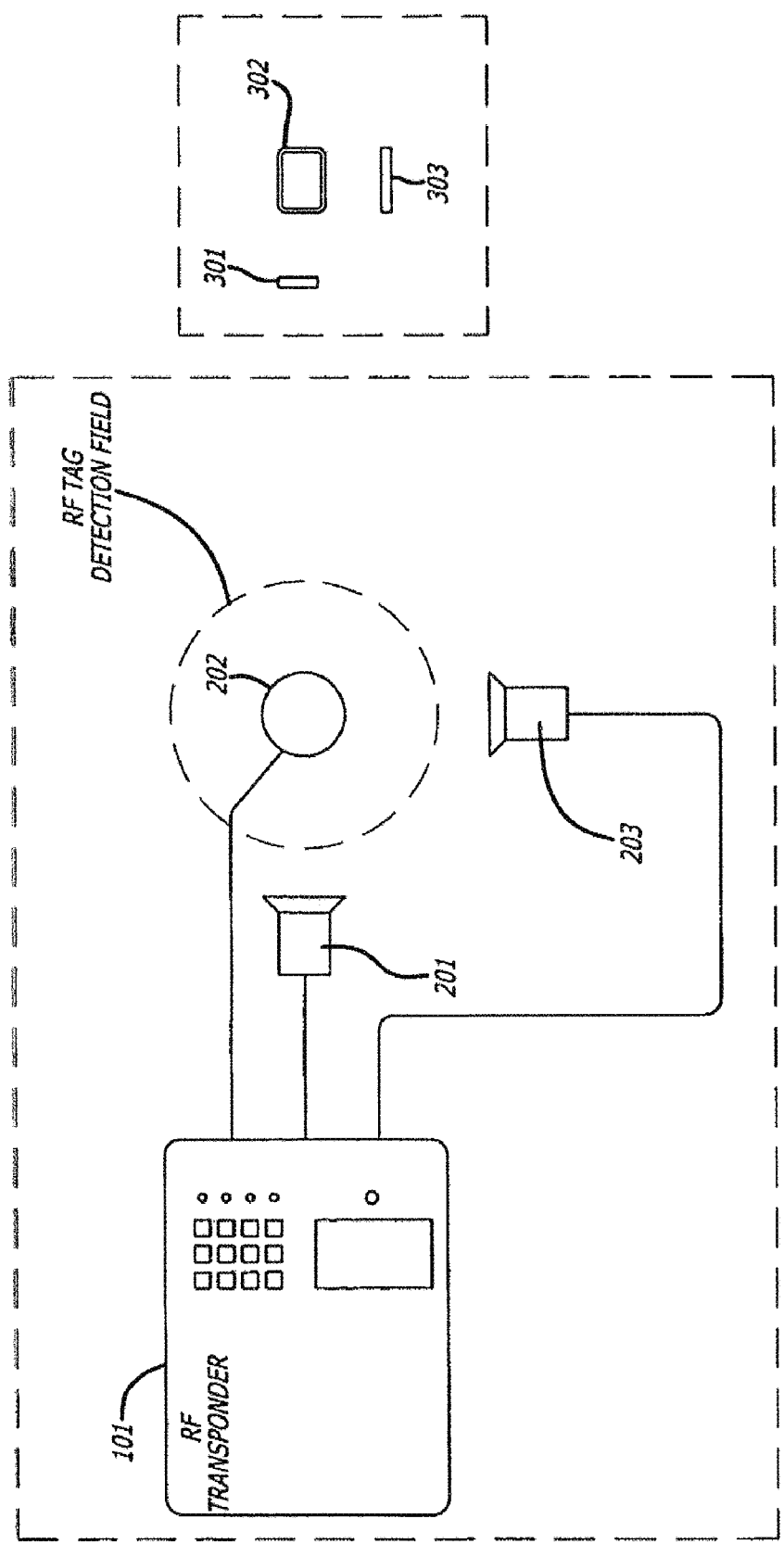
FIG. 9 is a schematic representation of an alternate embodiment of an RF transducer alignment system of the present disclosure illustrating a multi-axis alignment system having three RF antennas and three RF tags in an "x", "y", and "z" orientation.

FIG. 9 depicts an example embodiment and application of the present disclosure, wherein an application requiring the use of "x," "y," and "z" coordinates is illustrated, for example a medical instrumentation or where diagnosis or treatment procedures or equipment is concerned.

If item 101, an integrated RF means interrogator, is attached to a computerized (at some level) medical apparatus, the RF interrogator 101 can, at a minimum, provide certain information about the location and critical alignment of items 301-303, certain RF tags arranged in "x," "y," and "z" coordinates by means of items 201-203, remote RF antenna means, also arranged in "x," "y," and "z" coordinates, wherein the RF antenna 201 is responsive only to the RF tag 301, and vise versa; and wherein the RF antenna 202 is responsive only to the RF tag 302 and vise versa; and wherein the RF antenna 203 is responsive only to the RF tag 303 and vise versa, providing for an enhanced RF transducer alignment system.

Such a system could be attached to, or about, a (perhaps semi-automated) radiation device and apparatus for cancer treatment. Variant embodiment RF tags placed on a given patient's body or about the body could allow, at a minimum, for precise alignment of the radiation device and apparatus so as to eventually execute a reliably placed radiation treatment.

Additionally, RF antennas 201-203 could be fabricated such that each RF antenna is adjustable along its assigned, dominant axis, providing for instances wherein the "x," "y," and "z" RF tags might be positioned in obtuse ways to each other, and therefore the RF tags might not necessarily be positioned in a purely spherical or geometric way about each other, and in fact may reside at unequal distances from each other.

Additionally still, RF antennas 201-203 could be fabricated such that each or all the RF antennas are adjustable about a given or expected RF tag detection field (see FIG. 9, upper middle nomenclature and dashed circle), wherein standard "x," "y," and "z" coordinates (purely horizontal "x," and "z," and purely vertical "y," might not be practical), and thus the RF antennas might accommodate being repositionable about three-dimensional space.

FIG. 10 depicts an example embodiment and application of the present disclosure wherein digital radiography is utilized. Specifically illustrated is a top-view of a dental digital imaging sensor 600 wherein also is illustrated a slip-on RF tag 304. The RF tag 304 could be a reusable device, and it would slip over the digital imaging sensor 600, a customarily non-reusable device, so that one may obtain exacting x-ray images by means provided by the RF tag 304 and the present disclosure.

FIG. 11 depicts an example embodiment and application of the present disclosure wherein a portable RF interrogator apparatus 703 is shown constructed, looking similar in nature to a given field-applicable metal detector device, wherein a handle 701 and a modified remote RF antenna 702 labeled "multi-form antenna coil" provides for RF tag detection by means of two predeterminedly sized carrier transmit/data receive coils, each possibly operating at differing frequencies, and possibly at differing power levels, by means of predetermined RF waveform drive signals DRIVE 1 and DRIVE 2, and wherein each RF antenna might be able to be used independently from the other or in synchronicity with each other.

Item 702-A, the larger of the carrier transmit/data receive coils, might generally provide for broad-field RF tag detection only, wherein item 702-B, the smaller of the carrier transmit/data receive coils, might generally provide for near-field RF tag detection as well as critical alignment RF tag detection.

Figure 12A:
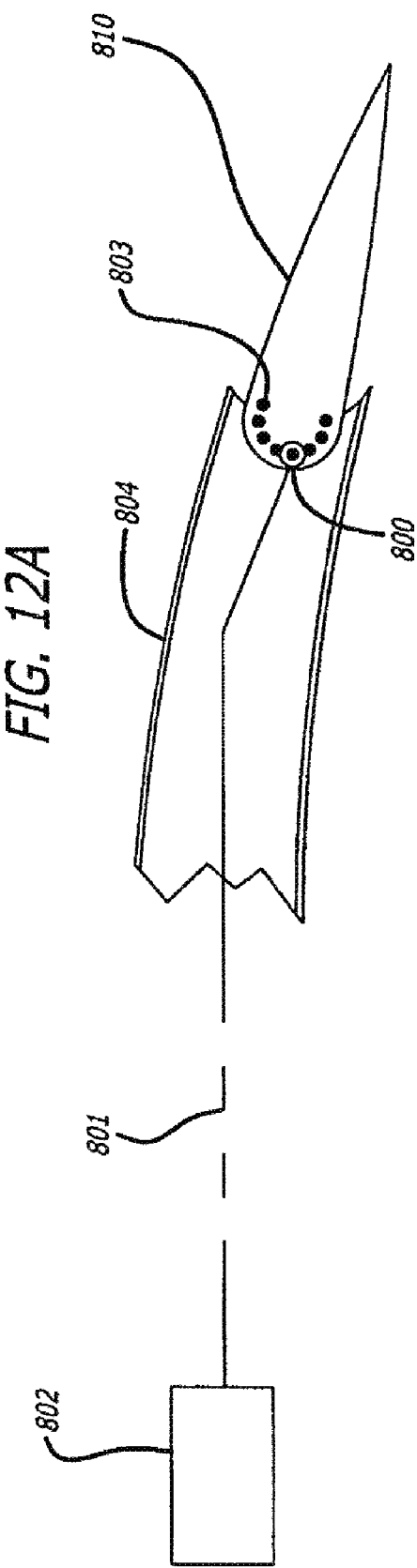
FIGS. 12A and 12B are schematic representations of an alternate embodiment of an RF transducer alignment system of the present disclosure illustrating a multi-point RF tag detection and alignment feedback system for a winged aircraft.
Figure 12B:
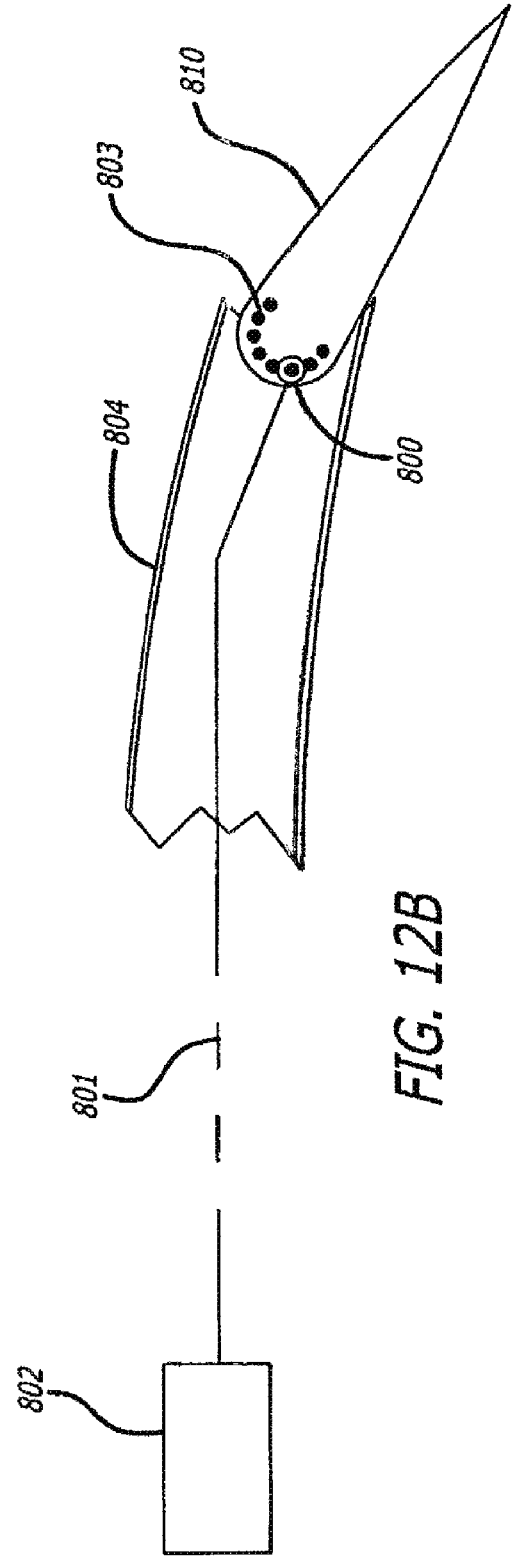

FIG. 12 depicts an example embodiment and application of the present disclosure wherein a multi-RF tag arrangement, via items 803, is utilized with an RF antenna 800 so as to identify an exacting attitude of an alterable-position flight-surface of an airfoil 804, wherein item 810, the alterable-position flight-surface of the top-most figure, depicts a "level flight" position and attitude, and wherein item 810, also the alterable-position flight-surface, but illustrated in the bottom-most figure, depicts a "dive or descend" position and attitude.

An umbilical cable 801 provides certain predetermined signals to and from a given flight surface control computer 802, which has the built-in capability to critically identify the position of all flight surfaces of a given aircraft. Since the RF tags need not protrude from the flight surfaces, and since they are not prone to wear, contamination, or rust, etc., and need no outside attached power source, they, with an alternate embodiment of the present disclosure, are configured to interface with the flight surface control computer, 802, provide an ideal platform whereby a pilot, and/or certain nav-computers, can critically monitor all movable flight surfaces, and potentially, by means of the nav-computers software, provide "safing" measures when "expected" or "normal," etc. RF tag signals fail to manifest from the RF antenna devices 800.

Figure 13:
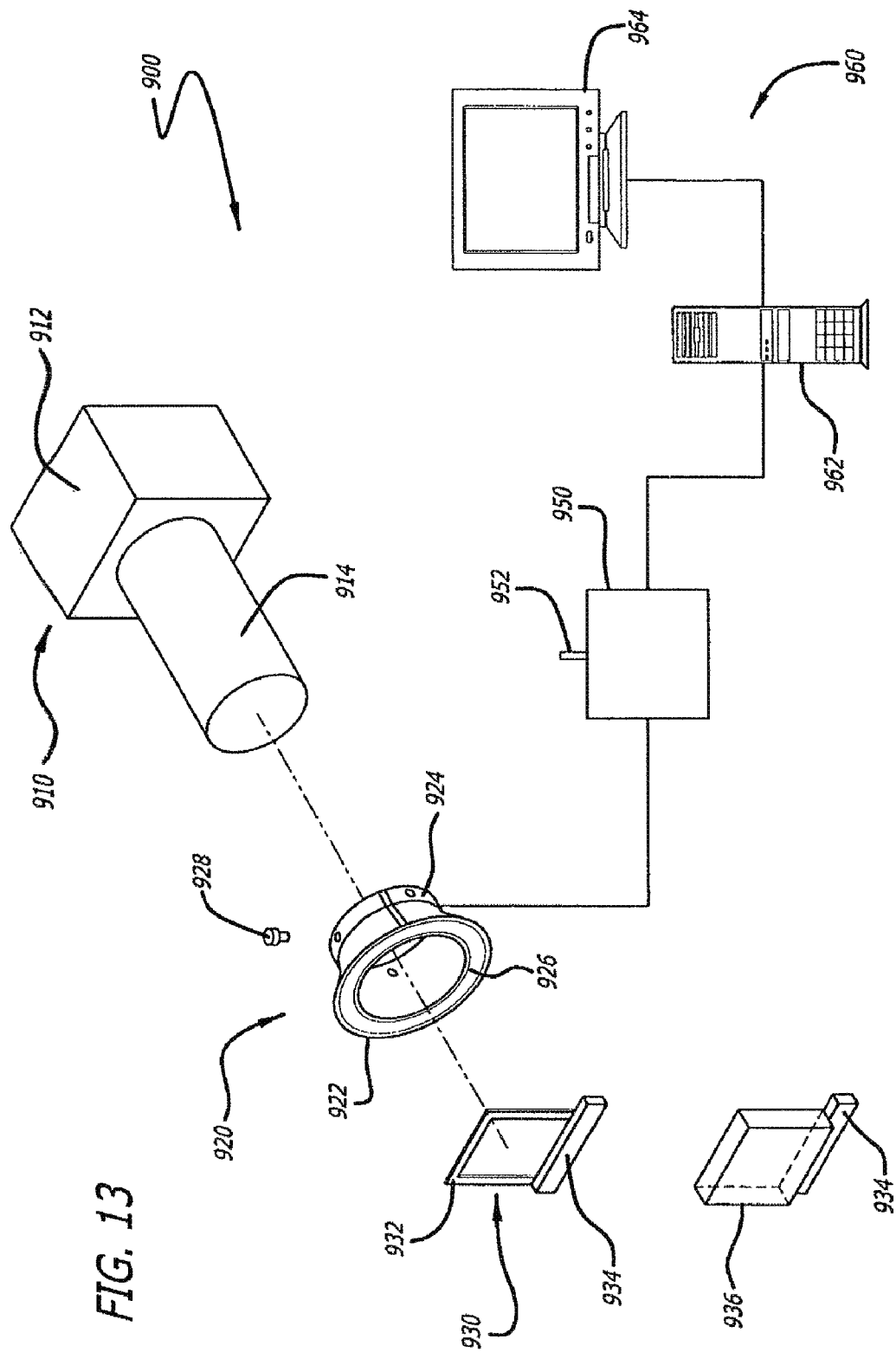
FIG. 13 is a schematic representation of the RFID alignment system of the present disclosure applied to a dental x-ray apparatus.

Referring now to FIG. 13, the RFID alignment system 900 of the present disclosure may be applied to a dental x-ray apparatus having an x-ray emitter 912 and extension tube 914. An RF assembly 920 is configured to be removably or fixedly installed on the extension tube of the x-ray apparatus. The antenna assembly includes a hollow cylindrical portion 924 configured to concentrically slide or otherwise attach to the x-ray extension tube. The portion of the antenna that attaches to the extension tube may be configured with an attachment device, such as screws 928, for fixing the antenna to the x-ray tube. The antenna assembly may further include a flange 922 or may be otherwise configured to contain an antenna or coil 926. Seating the coil in the holder should be precise and concentric so as to establish proper alignment between the x-ray emitter and the film or sensor. The coil may be glued into the flange or seat of the antenna assembly and a face plate may be provided so that the coil is not exposed to the environment. Channels may be provided within the assembly to house the wires from the coil to a antenna control assembly 950. An indicator 952, such as a plastic non-conductive lamp, LED or other device, may be mounted at or near the antenna control assembly 950. The antenna control assembly may be operably connected to a computer system 960. Such a computer system may include a microprocessor 962 and display device 964. The computer system may be used to process the identification from the RF tag and associated patient information.

The dental x-ray system further includes an imaging device 930 having a frame 932 for holding the RFID tag, coil antenna and a film (sensor) holder assembly (bitewing) 934. The tag, coil antenna and x-ray film may also be contained within a standard dental film holder 936. The film holder may be manufactured so that it contains an RFID tag with the antenna running around the perimeter of the film. The RF tag may be programmed to contain patient information, such as social security number, invoice number, time, date, tooth location, and other dental records. The tag antenna may be configured so that it will not cover the surface of the film or sensor and may lay coplanar around the film (or sensor) in a circular or rectangular shape, leaving the surface of the film or sensor clear for the image. Then tag antenna 932 may be part of the film cover 930. The windings that make up the antenna may be cast into the plastic containing the microchip itself. The microchip may contain a unique number that can be assigned to the patient via the computer system. Alternatively, the tag antenna may be placed between plastic sheets that are glued to the film or sensor surface. A software package may be provided for the computer system that communicates through standard serial communication protocols to the leader control assembly.

In operation, the antenna assembly 920 may be installed on the extension tube 914 of the x-ray apparatus 910. The film holder assembly 930 is inserted into the patient's mouth and the x-ray operator powers the control system 950. When the antenna assembly 920 and the tag assembly 930 are aligned perpendicular and concentric, an indicator light 952 shows that the system is aligned and the radiograph is ready to be taken. The antenna will power the tag antenna only when the two are exactly perpendicular and concentric to one another. When this occurs, the indicator light turns on indicating alignment of the two devices (antennas), and at this time the best alignment is achieved. Alternatively, the computer system may be configured such that it inhibits powering of the x-ray emitter until such alignment occurs.

Thus and in conclusion, there has been demonstrated a versatile, inventive, economical, and beneficial RFID interrogator alignment system, providing for broadened operational functionality, and altogether new RFID applications, independent of any given embodiment. With such a beneficial and suitable design, with manifold applications with which to apply the present disclosure, wide use could not only result in a great deal of user-satisfaction and benefit, as well as improved manufacturers end-product(s), but in some instances, result in certain financial savings for the end-user or others.

While a particular form of the present disclosure has been illustrated and described, it will be apparent to those skilled in the art that various modifications can be made without departing from the inventive concept. Accordingly, it will be understood by those skilled in the art that certain changes in function, form, capacity, size, shape, and/or other detail may be made without departing or detracting from the spirit and scope of the present disclosure. Accordingly, it is not intended that the disclosure be limited except by the appended claims.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A radio frequency alignment apparatus, comprising:
   an interrogator configured to emit at least one interrogation signal within an area of alignment;
   at least one transponder configured to emit at least one radio frequency signal in response to the at least one interrogation signal from the interrogator; and
   the interrogator configured to receive the at least one radio frequency signal from the at least one transponder and to generate at least one signal that is processed to generate at least one of a detection signal and an alignment signal regarding the detection of the transponder and the relative orientation of the transponder and the interrogator to each other, respectively.

2. The apparatus of claim 1, further comprising an indicator configured to provide at least one of a visual and an audio indication of the detection and alignment.

3. The apparatus of claim 1 wherein the interrogator comprises:
   an analog front end circuit configured to process the at least one radio frequency signal from the at least one transponder and to generate one or more output signals;
   a microprocessor associated with the interrogator and configured to process the one or more output signals from the analog front end circuit;
   a memory associated with the microprocessor for storing data obtained from the at least one radio frequency signal as processed by the microprocessor; and
   wherein an indicator is coupled to the microprocessor for indicating at least the detection of the presence of the at least one transponder by the interrogator.

4. The apparatus of claim 1, further comprising an imaging device sensitive to x-rays coupled to the at least one transponder, the imaging device adapted to produce an image when in the presence of applied x-rays.

5. The apparatus of claim 4 wherein an x-ray emitter device is associated with the interrogator.

6. The apparatus of claim 1, further comprising an x-ray emitter device associated with the interrogator and an x-ray imaging device associated with the at least one transponder.

7. The apparatus of claim 1, further comprising a plurality of interrogators adapted to communicate with the at least one transponder.

8. The apparatus of claim 7, further comprising a plurality of transponders configured to communicate with the plurality of interrogators.

9. The apparatus of claim 1, further comprising:
   at least one amplifier configured to enhance a received at least one radio frequency signal from the at least one transponder to produce at least one amplified signal; and
   at least one filter for conditioning the at least one amplified signal.

10. A method for aligning first and second devices, comprising:
    emitting from an interrogator associated with the first device an electromagnetic field of flux;
    emitting a radio frequency signal from a transponder associated with the second device when the transponder detects the electromagnetic field of flux from the interrogator;
    detecting the radio frequency signal from the transponder when the first device is in a condition of alignment with the second device; and
    generating at least one of a detection signal when the radio frequency signal from the transponder is detected and an alignment signal when the first device is in a condition of alignment with the second device.

11. The method of claim 10, comprising moving the interrogator until the radio frequency signal from the transponder is detected.

12. The method of claim 10, comprising moving the transponder until the radio frequency signal from the a transponder is detected by the an interrogator.

13. The method of claim 10, further comprising:
    storing patient specific information and procedural and other data within the transponder;

formatting and serializing of the stored data within the transponder to modulate the radio frequency signal emitted by the transponder;

processing the detected radio frequency signal received from the transponder to obtain the stored patient specific information and procedural and other data;

processing the detected radio frequency signal from the transponder to obtain condition of alignment information between the first and the second devices; and displaying the patient specific information and procedural and other data.

14. The method of claim 10, further comprising:

placing the transponder associated with an x-ray sensitive imaging device in the mouth of a patient; and moving the interrogator, which is associated with an x-ray emitter, until the radio frequency signal from the transponder is detected.

15. A system for obtaining a dental x-ray, comprising:

an x-ray emissions device;

an interrogator associated with the x-ray emissions device and configured to emit an electromagnetic field of flux;

an imaging device sensitive to x-rays; and a transponder associated with the imaging device and configured to emit a radio frequency signal when excited by the electromagnetic field of flux from the interrogator;

wherein the interrogator is configured to detect the radio frequency signal from the transponder and to generate at least one of a detection signal when the interrogator detects the radio frequency signal and an alignment signal when there is an alignment condition between the an x-ray emissions device and the imaging device sensitive to x-rays.

16. The system of claim 15, further comprising an indicator configured to be activated when the interrogator detects the a radio frequency signal from the transponder.

17. The system of claim 15 wherein the x-ray emissions device is configured to inhibit the emission of x-rays until the interrogator detects the radio frequency signal from the transponder.

18. The system of claim 15 wherein the transponder is further configured to include within the radio frequency signal patient identification data.

19. The system of claim 18 wherein the interrogator comprises:

an analog front end circuit configured to process the radio frequency signal from the transponder and to generate an output signal;

a microprocessor associated with the interrogator and configured to process the output signal from the analog front end circuit; and a memory associated with the microprocessor for storing data obtained from the radio frequency signal as processed by the microprocessor;

wherein an indicator is coupled to the microprocessor for indicating at least the detection of the radio frequency signal from the transponder.

20. The system of claim 19 wherein the microprocessor is configured to activate the emission of x-rays by the x-ray emissions device when the interrogator detects a condition of alignment between the interrogator and the transponder.

21. The method of claim 10, comprising moving the interrogator until a desired condition of alignment to the transponder has been achieved.

22. The method of claim 10, comprising:

moving the transponder until a desired condition of alignment to the an interrogator has been achieved.

23. A system for identifying the attitude of a movable flight surface of an airfoil, comprising:

an antenna associated with the airfoil and configured to emit an electromagnetic field of flux;

at least one transponder associated with the movable surface and configured to emit a radio frequency signal when excited by the electromagnetic field of flux; and a computing device coupled to the antenna and adapted to generate a signal to the antenna to initiate the electromagnetic field of flux and to detect the radio frequency signal received on the antenna and to generate a movable flight surface position signal in response thereto.

24. The system of claim 23 wherein the computing device is adapted to generate safety signals when the movable flight surface is not within a normal condition or radio frequency signals are not received at the computing device.

25. The system of claim 23 wherein the computing device is configured to provide monitoring of the movable flight surface for a pilot.

26. The system of claim 23, comprising a plurality of transponders associated with the movable flight surface.

* * * * *